United States Patent
Albrecht et al.

(10) Patent No.: US 10,358,437 B2
(45) Date of Patent: Jul. 23, 2019

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Brian K. Albrecht, Cambridge, MA (US); Alexandre Cote, Cambridge, MA (US); Terry Crawford, South San Francisco, CA (US); Martin Duplessis, Cambridge, MA (US); Andrew Charles Good, Cambridge, MA (US); Yves LeBlanc, Cambridge, MA (US); Steven Magnuson, South San Francisco, CA (US); Christopher G. Nasveschuk, Cambridge, MA (US); Richard Pastor, South San Francisco, CA (US); F. Anthony Romero, South San Francisco, CA (US); Alexander M. Taylor, Cambridge, MA (US)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/449,706

(22) Filed: Mar. 3, 2017

(65) Prior Publication Data
US 2017/0334883 A1    Nov. 23, 2017

Related U.S. Application Data

(63) Continuation of application No. PCT/US2015/048174, filed on Sep. 2, 2015.

(60) Provisional application No. 62/046,770, filed on Sep. 5, 2014.

(51) Int. Cl.
| | |
|---|---|
| C07D 249/12 | (2006.01) |
| C07D 403/04 | (2006.01) |
| C07D 403/12 | (2006.01) |
| C07D 401/04 | (2006.01) |
| C07D 401/12 | (2006.01) |
| A61K 31/53 | (2006.01) |
| A61K 31/4196 | (2006.01) |
| A61P 35/00 | (2006.01) |
| C07D 253/075 | (2006.01) |
| A61K 45/06 | (2006.01) |

(52) U.S. Cl.
CPC .......... *C07D 403/12* (2013.01); *A61K 31/53* (2013.01); *A61K 45/06* (2013.01); *A61P 35/00* (2018.01); *C07D 249/12* (2013.01); *C07D 253/075* (2013.01); *C07D 401/04* (2013.01); *C07D 401/12* (2013.01); *C07D 403/04* (2013.01)

(58) Field of Classification Search
CPC .. C07D 403/04; C07D 403/12; C07D 249/12; A61K 31/53; A61K 31/4196; A61P 35/00
USPC ......................................... 544/182; 514/242
See application file for complete search history.

(56) References Cited

U.S. PATENT DOCUMENTS

| | | | |
|---|---|---|---|
| 5,591,743 A | 1/1997 | Patoiseau et al. | |
| 7,803,795 B2 | 9/2010 | Mevellec et al. | |
| 2013/0064770 A1* | 3/2013 | Newington .......... | C07D 209/14 424/1.89 |

(Continued)

FOREIGN PATENT DOCUMENTS

| | | |
|---|---|---|
| WO | 2006003147 A1 | 1/2006 |
| WO | 2010006962 A1 | 1/2010 |
| WO | 2011150183 A1 | 12/2011 |

(Continued)

OTHER PUBLICATIONS

Cecil Textbook of Medicine, edited by Bennet, J.C., and Plum F., 20th edition,vol. 1, 1004-1010, 1996.*

(Continued)

*Primary Examiner* — Venkataraman Balasubramanian
(74) *Attorney, Agent, or Firm* — Viksnins Harris Padys Malen LLP

(57) ABSTRACT

The present invention relates to methods for treating PCAF mediated disorders using a compound of formula (I) or a pharmaceutically acceptable salt thereof:

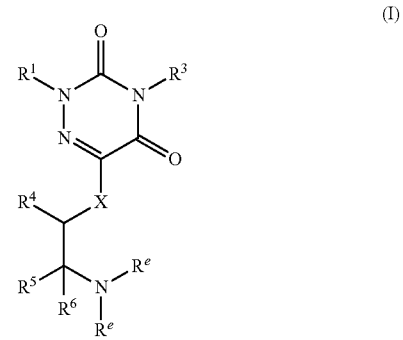

(I)

wherein $R^1$, $R^3$-$R^6$, X, and each $R^e$ have any of the values defined in the specification. Also included are novel compounds of formula (I) and salts thereof, as well as pharmaceutical compositions comprising a compound of formula (I) or a pharmaceutically acceptable salt thereof.

9 Claims, No Drawings

(56) References Cited

U.S. PATENT DOCUMENTS

| | | |
|---|---|---|
| 2014/0275069 A1 | 9/2014 | Jantos et al. |
| 2017/0275289 A1 | 9/2017 | Albrecht et al. |

FOREIGN PATENT DOCUMENTS

| | | |
|---|---|---|
| WO | 2013092574 A1 | 6/2013 |
| WO | 2014068388 A1 | 5/2014 |
| WO | 2014144721 A2 | 9/2014 |
| WO | 2016112298 A1 | 7/2016 |

OTHER PUBLICATIONS

Freshney et al., Culture of Animal Cells, A Manual of Basic Technique, Alan R. Liss, Inc., 1983, New York, p. 4.*
Dernner et al., Bio/Technology, 1994, 12:320.*
Golub et al., Science, 286, 531-537, 1999.*
Pcconnpound-selected items 14, Create Date Jul. 21, 2009 to Oct. 23, 2012.*
Pcconnpound-selected items 1-200 of 518, Create Date Jul. 21, 2009 to Oct. 23, 2012.*
Pcconnpound-selected items 201-400 of 518, Create Date Jul. 21, 2009 to Oct. 23, 2012.*
Pcconnpound-selected items 401-518 of 518, Create Date Jul. 21, 2009 to Oct. 23, 2012.*
Garnier, et al., "BET bromodomain inhibitors: a patent review", Expert Opinion on Therapeutic Patents vol. 24 (2), 185-199 (2014).
Jeanmougin, "The bromodomain revisited", Trends Biochem Sci 22(5), 151-153 (1997).
Malinka, et al., "New derivatives of pyrrolo[3,4-d]pyridazinone and their anticancer effects", IL Farmaco 59, 457-462 (2004).
Manzo, et al., "Histone acetyltransferase inhibitors and preclinical studies", Expert Opin Ther Patents 19(6), 761-774 (2009).
Muller, et al., "Bromodomains as therapeutic targets", Expert Rev Mol Med 13 (29), 1-21 (2011).
Patent Cooperation Treaty, International Searching Authority, Search Report and Written Opinion for PCT/US2015/048174, 9 pages, dated Oct. 22, 2015.
Pring, et al., "Synthesis and Mechanism of Formation of 2,3-Dialkyl-1,2,3,4-tetrahydrophthalazine-1,4-diones by Utilizing an O—N Rearrangement of 1-Alkoxy-3-alkyl-3,4-dihydrophthalazin-4-ones", Acta Chemica Scandinavica 27, 1891-1899 (1973).
Prinjha, et al., "Place your BETs: the therapeutic potential of bromodomains", Trends Pharm Sci 33(3), 146-153 (2012).
Struhl, "Histone acetylation and transcriptional regulatory mechanisms", Genes Dev 12 (5), 599-606 (1989).
Tamkun, et al., "brahma: a regulator of *Drosophila homeotic* genes structurally related to the yeast transcriptional activator SNF2/SWI2", Cell 68, 561-572 (1992).
Venkatesh, et al., "Role of the Development Scientist in Compound Lead Selection and Optimization", Journal of Pharmaceutical Sciences 89 (2), 145-154 (2000).
Cingolani, et al., "Su Alcuni Derivati Dell Acido Orotico. Ammidi, Idrazoni, Idrazine", Farmaco, Edizione Scientitica 20(4), 259-269 (1965). [English Summary.].
Elagawany, et al., "Design, synthesis, and molecular modelling of pyridazinone and phthalazinone derivatives as protein kinases inhibitors", Bioorganic & Medicinal Chemistry Letters 23, 2007-2013 (2013).
Kormendy, "Aminophthalazinone Derivatives, I", Acta Chimica Academiae Scientiarum Hungaricae 88(2), 129-136 (1976).
Sladowska, et al., "Investigations on the synthesis and properties of 4-aminosubstituted 2,6,7-trimethyl-1,5-dioxo-1,2,5,6-tetrahydropyrido[3,4-d]pyridazines", Farmaco 53(7), 475-479 (1998).
Dekker, et al., "Inhibition of the PCAF histone acetyl transferase and cell proliferation by isothiazolones", Bioorganic & Medicinal Chemisry 17, 460-466 (2009).
Alekseeva, I, et al., "Anomalous Nucleosides and Related Compounds XXXI.* N,N'-Bis(6-AZA-5-URACILYL) Ethylenediamine and its Diglucopyranoside", Institute of Molecular Biology and Genetics, Academy of Sciences of the Ukrainian SSR, Kiev 252627. Translated from Khimiya Geterotsiklicheskikh Soedinenii, No. 11, 1561-1563, Nov. 1978. Original article submitted Nov. 9, 1977; revision Apr. 4, 1978.
Chernetskii, V, et al., "Anomalous Nucleosides and Related Compounds XI. Amino Acid Derivatives of 6-Azauracil*", Khimiya Geterotsiklicheskikh Soedinenii 5(1), 173-174 (1969).
Chinese Office Action for Application No. 201580059718.0, 9 pages, Feb. 14, 2019. [English Translation].
Database Registry, RN 1522308-54-8, 1 page, Jan. 15, 2014.
Database Registry, RN 1525602-00-9, 1 page, Jan. 20, 2014.
Database Registry, RN 152561-69-1, 1 page, Jan. 20, 2014.
Database Registry, RN 152855-84-1, 1 page, Feb. 23, 2014.
Database Registry, RN 1538195-91-3, 1 page, Feb. 6, 2014.
Database Registry, RN 1544908-62-4, 1 page, Feb. 16, 2014.
Database Registry, RN 1545236-02-9, 1 page, Feb. 1, 2014.
Database Registry, RN 1545371-12-7, 1 page, Feb. 16, 2014.
Database Registry, RN 1551487-08-1, 1 page, Feb. 20, 2014.
Database Registry, RN 1552029-91-0, 1 page, Feb. 21, 2014.
Database Registry, RN 1552661-69-4, 1 page, Feb. 23, 2014.
Database Registry, RN 1552890-36-4, 1 page, Feb. 23, 2014.
Database Registry, RN 1560566-34-4, 1 page, Mar. 3, 2014.
Database Registry, RN 1561083-97-3, 1 page, Mar. 3, 2014.
Database Registry, RN 1561467-71-7, 1 page, Mar. 4, 2014.
Database Registry, RN 1561981-84-7, 1 page, Mar. 4, 2014.
Database Registry, RN 159566-67-8, 1 page, May 2, 2014.
Database Registry, RN 1597880-18-6, 1 page, May 6, 2014.
Database Registry, RN 1597934-50-3, 1 page, May 6, 2014.
Database Registry, RN 1604292-81-0, 1 page, May 14, 2014.
Database Registry, RN 1604293-02-8, 1 page, May 14, 2014.
Database Registry, RN 160490-50-7, 1 page, Mar. 3, 2014.
Database Registry, RN 160825-80-0, 1 page, Mar. 3, 2014.
Database Registry, RN 950033-03-1, 1 page, Oct. 10, 2007.

* cited by examiner

THERAPEUTIC COMPOUNDS AND USES THEREOF

CROSS-REFERENCE TO RELATED APPLICATION

This application is a continuation of International Application serial no. PCT/US2015/048174, filed Sep. 2, 2015, which claims the benefit of priority of U.S. application Ser. No. 62/046,770, filed Sep. 5, 2014, which applications are herein incorporated by reference.

TECHNICAL FIELD OF THE INVENTION

The present invention relates to compounds useful as inhibitors of P300/CBP-associated factor (PCAF) as well as its closely related homolog GCN5, and methods of treating cancer using such inhibitors.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., *Genes Dev.*, 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., *Trends Biochem. Sci.*, 1997, 22, 5, 151-153; and Tamkun J. W., et al., *Cell*, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., *Trends Pharm. Sci.*, 33(3):146-153 (2012) and Muller et al., *Expert Rev.*, 13(29):1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. This is highlighted by the observation that mutations in bromodomain-containing proteins are linked to cancer, as well as immune and neurologic dysfunction. Hence, the selective inhibition of bromodomains across a specific family, such as the selective inhibition of a bromodomain of PCAF, creates varied opportunities as novel therapeutic agents in human dysfunction.

There is a need for treatments for cancer, immunological disorders, and other PCAF bromodomain related diseases. There is also a need for treatments for GCN5 mediaed disorders.

SUMMARY OF THE INVENTION

One aspect includes a method for treating a PCAF mediated disorder or a GCN5 mediated disorder in an animal (e.g., a mammal such as a human) comprising administering to the animal a compound of formula (I), or a pharmaceutically acceptable salt thereof:

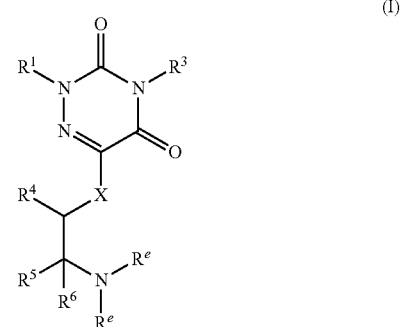

(I)

wherein:
$R^1$ is selected from the group consisting of H, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, amino, hydroxy, and $C_{1-6}$alkoxy;

X is $N(R^a)$;

$R^a$ is independently selected from the group consisting of hydrogen, $C_{1-6}$alkyl, $C_{2-6}$alkenyl, $C_{2-6}$alkynyl, $C_{1-6}$alkoxy, and carbocyclyl, wherein each $C_{1-6}$alkyl, $C_{2-6}$alkenyl, $C_{2-6}$alkynyl, $C_{1-6}$alkoxy, and carbocyclyl is optionally substituted with one or more groups independently selected from the group consisting of oxo, halo, amino, hydroxy, $C_{1-6}$alkoxy, and $C_1$-$C_6$ alkyl that is optionally substituted with one or more groups independently selected from oxo and halo; or $R^a$ and one $R^e$ taken together with the atoms to which they are attached form a 5-7 membered heterocyclyl, which 5-7 membered heterocyclyl is optionally substituted with one or more groups $R^b$; or $R^a$ and $R^4$ taken together with the atoms to which they are attached form a 5-7 membered heterocyclyl, which 5-7 membered heterocyclyl is optionally substituted with one or more groups $R^b$; or $R^a$ and $R^5$ taken together with the atoms to which they are attached form a 5-7 membered heterocyclyl, which 5-7 membered heterocyclyl is optionally substituted with one or more groups $R^b$;

each $R^b$ is independently selected from the group consisting of hydrogen, halo, oxo, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo;

$R^3$ is selected from the group consisting of H, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^f)_2$, —CN, —$C(O)N(R^f)_2$, —S(O)—$N(R^f)_2$, —$S(O)_2$—$N(R^f)_2$, —O—$R^f$, —S—$R^f$, —O—C(O)—$R^f$, —C(O)—$R^f$, —C(O)—$OR^f$, —S(O)—$R^f$, —$S(O)_2$—$R^f$, —$N(R^f)$—C(O)—$R^f$, —$N(R^f)$—S(O)—$R^f$, —$N(R^f)$—C(O)—$N(R^f)_2$, and —$N(R^f)$—$S(O)_2$—$R^f$;

$R^4$ and $R^5$ are each independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups $R^c$; or $R^4$ and $R^5$ taken together with the atoms to which they are attached form a carbocyclyl or heterocyclyl, which carbocyclyl and heterocyclyl is optionally substituted with one or more groups $R^c$;

$R^6$ is selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups $R^f$; or $R^6$ and $R^5$ taken together with the atoms to which they are attached form a carbocyclyl or heterocyclyl, which carbocyclyl and heterocyclyl is optionally substituted with one or more groups $R^f$;

each $R^c$ is independently selected from the group consisting of $C_{1-6}$alkyl, $C_{2-6}$alkenyl, $C_{2-6}$alkynyl, carbocyclyl, heterocyclyl, oxo, halo, —$NO_2$, —$N(R^d)_2$, —CN, —C(O)—N$(R^d)_2$, —S(O)—$N(R^d)_2$, —$S(O)_2$—$N(R^d)_2$, —O—$R^d$, —S—$R^c$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^d)_2$, —CN, —C(O)—$N(R^d)_2$, —S(O)—$N(R^d)_2$, —$S(O)_2$—N$(R^d)_2$, —O—$R^d$, —S—$R^d$, —O—C(O)—$R^d$, —C(O)—$R^d$, —C(O)—O—$R^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$;

each $R^d$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more $R^k$; or two $R^d$ are taken together with the nitrogen to which they are attached to form a heterocyclyl that is optionally substituted with one or more $R^k$;

each $R^e$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo;

or two $R^e$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

or one $R^e$ taken together with $R^4$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from the group consisting of oxo, halo, amino, hydroxy, $C_{1-6}$alkoxy and carbocyclyl;

or one $R^e$ taken together with $R^5$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from oxo, halo, amino, hydroxy, $C_{1-6}$alkoxy and carbocyclyl;

each $R^f$ is independently selected from the group consisting of $C_{1-6}$alkyl, $C_{2-6}$alkenyl, $C_{2-6}$alkynyl, carbocyclyl, heterocyclyl, oxo, halo, —$NO_2$, —$N(R^g)_2$, —CN, —C(O)—N$(R^g)_2$, —S(O)—$N(R^g)_2$, —$S(O)_2$—$N(R^g)_2$, —O—$R^g$, —S—$R^g$, —O—C(O)—$R^g$, —C(O)—$R^g$, —C(O)—$OR^g$, —S(O)—$R^g$, —$S(O)_2$—$R^g$, —$N(R^g)$—C(O)—$R^g$, —$N(R^g)$—S(O)—$R^g$, —$N(R^g)$—C(O)—$N(R^g)_2$, and —$N(R^g)$—$S(O)_2$—$R^g$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^g)_2$, —CN, —C(O)—$N(R^g)_2$, —S(O)—$N(R^g)_2$, —$S(O)_2$—N$(R^g)_2$, —O—$R^g$, —S—$R^g$, —O—C(O)—$R^g$, —C(O)—$R^g$, —C(O)—O—$R^g$, —S(O)—$R^g$, —$S(O)_2$—$R^g$, —$N(R^g)$—C(O)—$R^g$, —$N(R^g)$—S(O)—$R^g$, —$N(R^g)$—C(O)—$N(R^g)_2$, and —$N(R^g)$—$S(O)_2$—$R^g$;

each $R^g$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^g$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo.

each $R^k$ is independently selected from the group consisting of $C_{1-6}$alkyl, $C_{2-6}$alkenyl, $C_{2-6}$alkynyl, carbocyclyl, heterocyclyl, oxo, halo, —$NO_2$, —$N(R^m)_2$, —CN, —C(O)—$N(R^m)_2$, —S(O)—$N(R^m)_2$, —S(O)$_2$—$N(R^m)_2$, —O—$R^m$, —S—$R^m$, —O—C(O)—$R^m$, —C(O)—$R^m$, —C(O)—O$R^m$, —S(O)—$R^m$, —S(O)$_2$—$R^m$, —$N(R^m)$—C(O)—$R^m$, —$N(R^m)$—S(O)—$R^m$, —$N(R^m)$—C(O)—$N(R^m)_2$, and —$N(R^m)$—S(O)$_2$—$R^m$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^m)_2$, —CN, —C(O)—$N(R^m)_2$, —S(O)—$N(R^m)_2$, —S(O)$_2$—$N(R^m)_2$, —O—$R^m$, —S—$R^m$, —O—C(O)—$R^m$, —C(O)—$R^m$, —C(O)—O—$R^m$, —S(O)—$R^m$, —S(O)$_2$—$R^m$, —$N(R^m)$—C(O)—$R^m$, —$N(R^m)$—S(O)—$R^m$, —$N(R^m)$—C(O)—$N(R^m)_2$, and —$N(R^m)$—S(O)$_2$—$R^m$; and each $R^m$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^m$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo.

Another aspect includes a method for treating a PCAF mediated disorder or a GCN5 mediated disorder in an animal (e.g., a mammal such as a human) comprising administering to the animal a compound of formula (I), or a pharmaceutically acceptable salt thereof, wherein the compound of formula (I) is selected from the group consisting of:

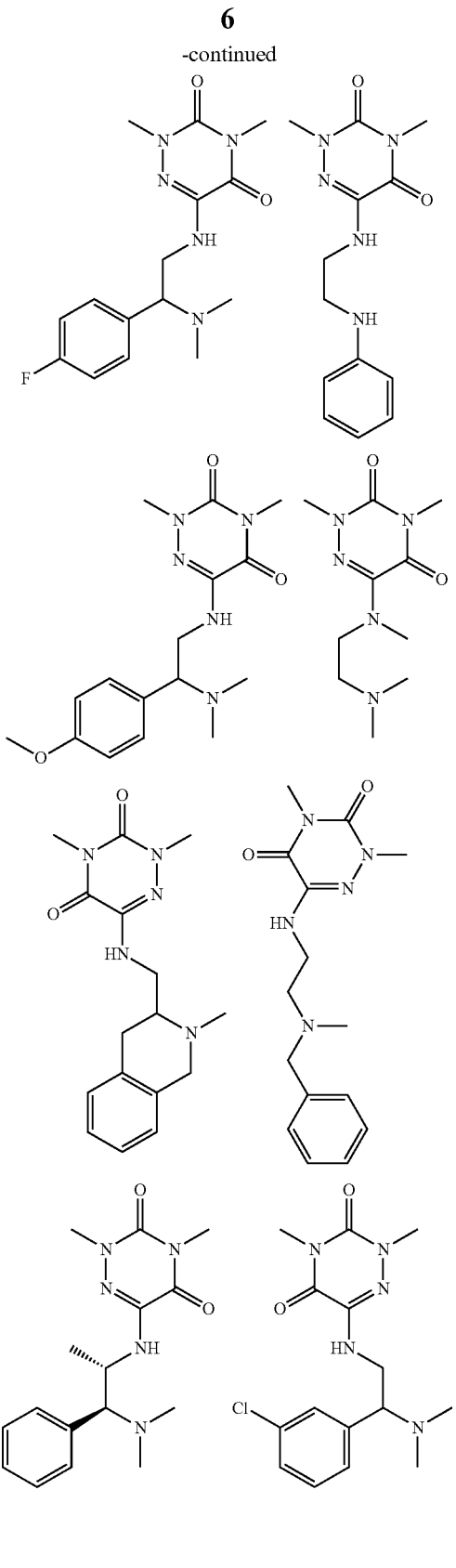

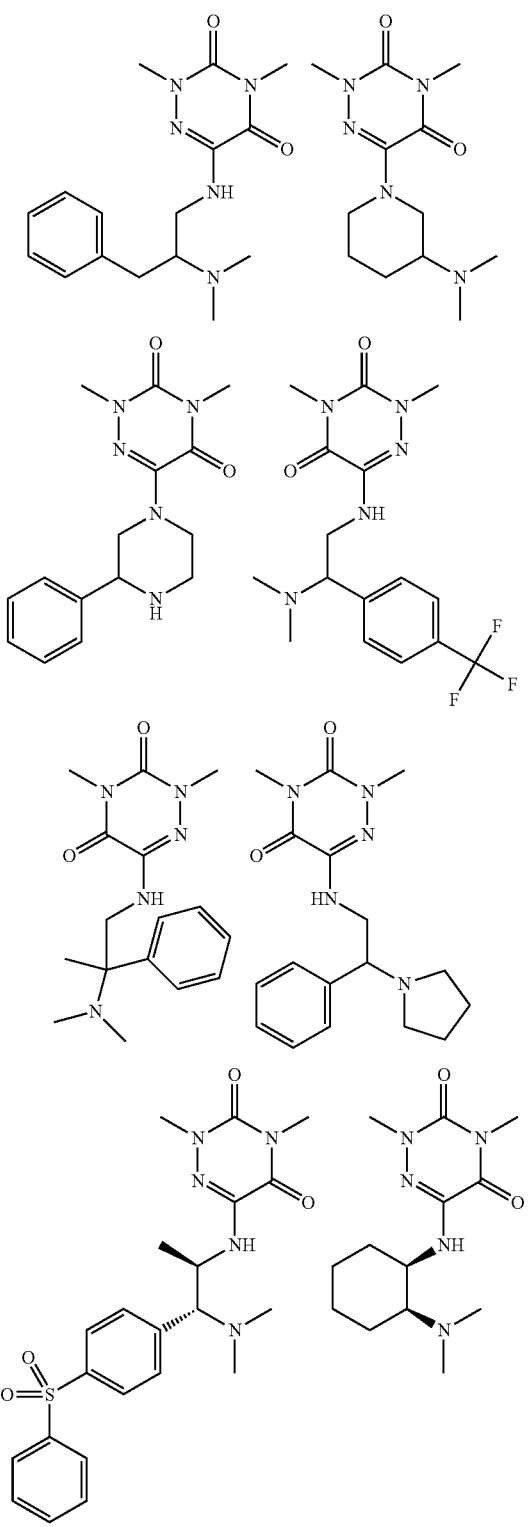

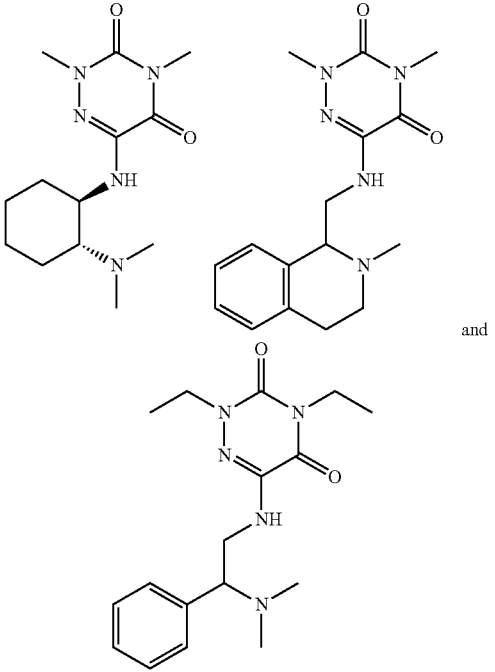

and

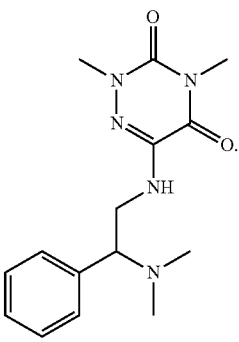 [SMILES: CN(C)C(CNc1nn(C)c(=O)n(C)c1=O)c1ccccc1]

Another aspect includes a method for treating a PCAF mediated disorder or a GCN5 mediated disorder in an animal (e.g., a mammal such as a human) comprising administering to the animal a compound of formula (I), or a pharmaceutically acceptable salt thereof, wherein the compound of formula (I) is:

Another aspect includes a composition comprising a compound of formula (I) or a pharmaceutically acceptable salt thereof, and a pharmaceutically acceptable adjuvant, carrier, or vehicle.

Another aspect includes a compound of formula (I) or a pharmaceutically acceptable salt thereof for use in medical therapy.

Another aspect includes a compound of formula (I) or a pharmaceutically acceptable salt thereof for the prophylactic or therapeutic treatment of a PCAF mediated disorder.

Another aspect includes the use of a compound of formula (I) or a pharmaceutically acceptable salt thereof to prepare a medicament for treating a PCAF mediated disorder in an animal (e.g., a mammal such as a human).

Another aspect includes compounds for the study of PCAF.

Another aspect includes novel compounds of formula (I) and salts thereof.

Another aspect includes a method of a) increasing efficacy of a cancer treatment comprising a cytotoxic agent in an animal (e.g., a mammal such as a human), b) delaying or preventing development of cancer resistance to a cytotoxic agent in an animal (e.g., a mammal such as a human), or c) extending the duration of response to a cancer therapy in an animal (e.g., a mammal such as a human) comprising administering to the animal an effective amount of a compound of formula (I) or a pharmaceutically acceptable salt thereof.

Another aspect includes a compound of formula (I) or a pharmaceutically acceptable salt thereof as described in claim 1 for a) increasing efficacy of a cancer treatment comprising a cytotoxic agent in an animal (e.g., a mammal such as a human), b) delaying or preventing development of cancer resistance to a cytotoxic agent in an animal (e.g., a mammal such as a human), or c) extending the duration of response to a cancer therapy in an animal (e.g., a mammal such as a human).

Another aspect includes the use of a compound of formula (I) or a pharmaceutically acceptable salt thereof to prepare a medicament for a) increasing efficacy of a cancer treatment comprising a cytotoxic agent in an animal (e.g., a mammal such as a human), b) delaying or preventing development of cancer resistance to a cytotoxic agent in an animal (e.g., a mammal such as a human), or c) extending the duration of response to a cancer therapy in an animal (e.g., a mammal such as a human).

Another aspect includes a method of treating cancer in an individual (e.g., a patient) comprising administering to the individual (a) a compound of formula (I) or a pharmaceutically acceptable salt thereof and (b) a cytotoxic agent.

Another aspect includes a compound of formula (I) or a pharmaceutically acceptable salt thereof for the prophylactic or therapeutic treatment of cancer in combination with a cytotoxic agent.

Another aspect includes the use of a compound of formula (I) or a pharmaceutically acceptable salt thereof to prepare a medicament for treating cancer in combination with a cytotoxic agent.

Another aspect includes synthetic intermediates and synthetic processes disclosed herein that are useful for preparing a compound of formula (I) or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75$^{th}$ Ed.

Unless otherwise stated, compounds of formula I include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included. Additionally, unless otherwise stated, structures depicted herein are also meant to include compounds that differ only in the presence of one or more isotopically enriched atoms. For example, compounds of formula I, wherein the independent replacement or enrichment of one or more hydrogen by deuterium or tritium, carbon by $^{13}$C— or $^{14}$C carbon, nitrogen by a $^{15}$N nitrogen, sulfur by a $^{33}$S, $^{34}$S or $^{36}$S sulfur, oxygen by a $^{17}$O or $^{18}$O oxygen, or fluorine by a $^{18}$F are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O.

The term "unsaturated", as used herein, means that a moiety has one or more units of unsaturation.

The term "carbocyclyl" used alone or as part of a larger moiety, refers to a saturated, partially unsaturated, or aromatic (e.g., aryl) ring system having 3 to 20 carbon atoms. In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In other embodiment, carbocyclyl, as a monocycle, includes $C_3$-$C_8$, $C_3$-$C_6$ or $C_5$-$C_6$. In another embodiment, carbocyclyl, as a bicycle, includes $C_7$-$C_{12}$. In another embodiment, carbocyclyl, as a Spiro system, includes $C_5$-$C_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and Spiro carbocyclyls include spiro[2.2]pentane, spiro[2.3] hexane, spiro[2.4]heptane, spiro[2.5]octane and spiro[4.5] decane. The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, heptyl, octyl, nonyl, decyl, undecyl and dodecyl.

The term "alkenyl," as used herein, denotes a linear or branched-chain hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl prop-1-ynyl (—C≡$CCH_3$), prop-2-ynyl (propargyl, —$CH_2$C≡CH), but-1-ynyl, but-2-ynyl and but-3-ynyl.

The term "alkoxy" refers to a linear or branched radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-20 carbon atoms ($C_6$-$C_{20}$ aryl). In another embodiment, aryl includes groups having 6-10 carbon atoms ($C_6$-$C_{10}$ aryl). Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted byone or more substituents described herein. A particular aryl is phenyl. In another embodiment aryl includes an aryl ring fused to one or more carbocyclic rings, such as indanyl, phthalimidyl, naphthimidyl, phenantriidinyl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. In some embodiments, the heteroaryl group is a $C_1$-$C_{20}$ heteroaryl group, where the heteroaryl ring contains 1-20 carbon atoms and the remaining ring atoms include one or more nitrogen, sulfur, or oxygen atoms. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, pyrid-2-yl N-oxide, and pyrazolo[4,3-c]pyridinyl. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono-, bi- or tri-cyclic.

As used herein, the term "heterocyclyl" refers to a "carbocyclyl" as defined herein, wherein one or more (e.g. 1, 2, 3, or 4) carbon atoms have been replaced with a heteroatom (e.g. O, N, or S). In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. A heterocyclyl can optionally be substituted with one or more substituents independently selected from those defined herein.

In one example, heterocyclyl includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl includes 1 to 4 heteroatoms. In another example, heterocyclyl includes 3- to 7-membered monocycles having one or more heteroatoms selected from nitrogen, sulfur or oxygen. In another example, heterocyclyl includes 4- to 6-membered monocycles having one or more heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In one example, the heterocyclyl group includes 0 to 3 double bonds. Any nitrogen or sulfur heteroatom may optionally be oxidized (e.g. NO, SO, $SO_2$), and any nitrogen heteroatom may optionally be quaternized (e.g. $[NR_4]^+Cl^-$, $[NR_4]^+OH^-$). Example heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

As used herein, the term "partially unsaturated" refers to a ring moiety that includes at least one double or triple bond between ring atoms but the ring moiety is not aromatic.

As used herein, the term "inhibitor" refers to a compound that binds to and inhibits PCAF with measurable affinity and activity. In certain embodiments, an inhibitor has an $IC_{50}$ or binding constant of less about 20 µM, less than about 1 µM, less than about 500 nM, less than about 100 nM, or less than about 10 nM.

The terms "measurable affinity" and "measurably inhibit," as used herein, refer to a measurable reduction in activity (e.g., reduction in recognition of lysine acetyl recognition of chromatin) of the bromodomain PCAF between: (i) a sample comprising a compound of formula I or composition thereof and such bromodomain, and (ii) an equivalent sample comprising such bromodomain, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula I is used to delay development of a disease or disorder or to slow the progression of a disease or disorder. Those individuals in need of treatment include those already with the condition or disorder as well as those prone to have the condition or disorder, (for example, through a genetic mutation or abberent expression of a gene or protein).

"PCAF bromodomain inhibitor" or refers to a compound that binds to the PCAF bromodomain and inhibits and/or reduces a biological activity of PCAF. In some embodiments, PCAF bromodomain inhibitor binds to PCAF primarily (e.g., solely) through contacts and/or interactions with the PCAF bromodomain. In some embodiments, PCAF bromodomain inhibitor substantially or completely inhibits the biological activity of PCAF. In some embodiments, the biological activity is binding of the bromodomain of PCAF to chromatin (e.g., histones associated with DNA) and/or another acetylated protein.

The terms "PCAF" and "P300/CBP-Associated Factor", "K(lysine)acetyltransferase 2B", "KAT2B", "Histone Acetylase PCAF", "Histone Acetyltransferase PCAF", "Lysine Acetyltransferase 2B", "P/CAF", "EC 2.3.1.48", "CAF", "CREBBP-Associated Factor", and "Histone Acetyltransferase KAT2B" as used herein, may be used interchangeably, and refer to any native PCAF from any vertebrate source, including mammals such as primates (e.g. humans) and rodents (e.g. mice and rats), unless otherwise indicated. The term encompasses "full-length" unprocessed PCAF as well as any form of PCAF that results from processing in the cell. The term also encompasses naturally occurring variants of PCAF, e.g. splice variants or allelic variants.

The term GCN5 includes GCN5L2, PCAF-b, KAT2A, STAF97, and the like.

As used herein, "a" or "an" means one or more, unless clearly indicated otherwise. As used herein, "another" means at least a second or more.

Exemplary Values

In one embodiment a compound of formula (I), or a salt thereof is provided:

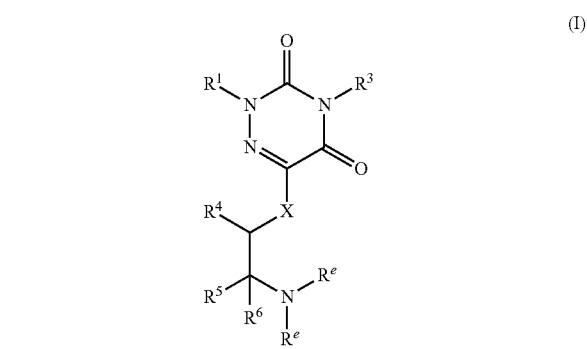

wherein:
$R^1$ is selected from the group consisting of H, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, amino, hydroxy, and $C_{1-6}$alkoxy;

X is $N(R^a)$;

$R^a$ is independently selected from the group consisting of hydrogen, $C_{1-6}$alkyl, $C_{2-6}$alkenyl, $C_{2-6}$alkynyl, $C_{1-6}$alkoxy, and carbocyclyl, wherein each $C_{1-6}$alkyl, $C_{2-6}$alkenyl, $C_{2-6}$alkynyl, $C_{1-6}$alkoxy, and carbocyclyl is optionally substituted with one or more groups independently selected from the group consisting of oxo, halo, amino, hydroxy, $C_{1-6}$alkoxy, and $C_1$-$C_6$ alkyl that is optionally substituted with one or more groups independently selected from oxo and halo; or $R^a$ and one $R^e$ taken together with the atoms to which they are attached form a 5-7 membered heterocyclyl, which 5-7 membered heterocyclyl is optionally substituted with one or more groups $R^b$; or $R^a$ and $R^4$ taken together with the atoms to which they are attached form a 5-7 membered heterocyclyl, which 5-7 membered heterocyclyl is optionally substituted with one or more groups $R^b$; or $R^a$ and $R^5$ taken together with the atoms to which they are attached form a 5-7 membered heterocyclyl, which 5-7 membered heterocyclyl is optionally substituted with one or more groups $R^b$;

each $R^b$ is independently selected from the group consisting of hydrogen, halo, oxo, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo;

$R^3$ is selected from the group consisting of H, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^f)_2$, —CN, —$C(O)N(R^f)_2$, —S(O)—$N(R^f)_2$, —$S(O)_2$—$N(R^f)_2$, —O—$R^f$, —S—$R^f$, —O—C(O)—$R^f$, —C(O)—$R^f$, —C(O)—$OR^f$, —S(O)—$R^f$, —$S(O)_2$—$R^f$, —$N(R^f)$—C(O)—$R^f$, —$N(R^f)$—S(O)—$R^f$, —$N(R^f)$—C(O)—$N(R^f)_2$, and —$N(R^f)$—$S(O)_2$—$R^f$;

$R^4$ and $R^5$ are each independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups $R^c$; or $R^4$ and $R^5$ taken together with the atoms to which they are attached form a carbocyclyl or heterocyclyl, which carbocyclyl and heterocyclyl is optionally substituted with one or more groups $R^c$;

$R^6$ is hydrogen or $C_{1-6}$alkyl;

each $R^c$ is independently selected from the group consisting of $C_{1-6}$alkyl, $C_{2-6}$alkenyl, $C_{2-6}$alkynyl, carbocyclyl, heterocyclyl, oxo, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^c$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, $N(R^d)$—S(O)—$R^d$, —$N(R^d)$—C(O)—$N(N^d)_2$, and —$N(R^d)$—$S(O)_2$—$R^d$, wherein any $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, —$NO_2$, —$N(R^d)_2$, —CN, —C(O)—$N(R^d)_2$, —S(O)—$N(R^d)_2$, —$S(O)_2$—N$(R^d)_2$, —O—$R^d$, —S—$R^d$, —O—C(O)—$R^d$, —C(O)—$R^d$, —C(O)—O—$R^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$;

each $R^d$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^d$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

each $R^e$ is independently selected from the group consisting of hydrogen, $C_{1-6}$alkyl, $C_{2-6}$alkenyl, $C_{2-6}$alkynyl, $C_{1-6}$alkoxy, carbocyclyl, and heterocyclyl, wherein each $C_{1-6}$, alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^e$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo; or one $R^e$ taken together with $R^4$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from the group consisting of oxo, halo, amino, hydroxy, $C_{1-6}$alkoxy and carbocyclyl; or one $R^e$ taken together with $R^5$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from oxo, halo, amino, hydroxy, $C_{1-6}$alkoxy and carbocyclyl; and each $R^f$ is independently selected from the group consisting of hydrogen, $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, $C_{1-6}$alkoxy, carbocyclyl, and heterocyclyl is optionally substituted with one or more groups independently selected from the group consisting of oxo, halo, amino, hydroxy, $C_{1-6}$alkoxy, carbocyclyl, heterocyclyl, and $C_1$-$C_6$ alkyl that is optionally substituted with one or more groups independently selected from the group consisting of oxo and halo; or two $R^f$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

provided that when $R^1$ is methyl, $R^3$ is methyl, X is N(H), $R^4$ is H, $R^6$ is H and each $R^e$ is H; then $R^5$ is not selected from the group consisting of H, propyl, cyclopropyl, isopropyl, ethyl, methyl, phenyl and 1-hydroxyethyl; and provided that when $R^1$ is methyl, $R^3$ is methyl, X is N(H), $R^4$ is H, $R^6$ is H and each $R^e$ is $CH_3$; then $R^5$ is not selected from the group consisting of H, phenyl, 2-methoxyphenyl, and methyl; and provided that when $R^1$ is methyl, $R^3$ is methyl, X is N(H), $R^5$ is H, $R^6$ is H and each $R^e$ is H; then $R^4$ is not selected from the group consisting of cyclopropyl, cyclohexyl, methyl, ethyl, butyl, isobutyl, propyl, isopropyl, phenyl, and benzyl; and provided that when $R^1$ is methyl, $R^3$ is methyl, X is N(H), $R^5$ is H, $R^6$ is H and each $R^e$ is $CH_3$; then $R^4$ is not selected from the group consisting of H, methyl, isopropyl, and isobutyl; and provided that when $R^1$ is methyl, $R^3$ is methyl, X is $N(R^a)$, $R^4$ is H, $R^5$ is H, $R^6$ is H and each $R^e$ is H; then $R^a$ is not selected from the group consisting of methyl, ethyl, propyl, isopropyl, cyclopropyl, butyl, cyclopentyl, cyclohexyl, 3-pentyl, and benzyl; and provided that when $R^1$ is H, $R^3$ is H, X is N(H), $R^4$ is H, $R^6$ is H and each $R^e$ is H; then $R^5$ is not selected from the group consisting of H, methyl, ethyl, propyl, cyclopropyl, isopropyl, 1-hydroxyethyl, and phenyl; and provided that when $R^1$ is H, $R^3$ is H, X is N(H), $R^4$ is H, $R^6$ is H and each $R^e$ is $CH_3$; then $R^5$ is not methyl; and provided that when $R^1$ is methyl, $R^3$ is methyl, X is N(H), $R^4$ is H, $R^6$ is H and $R^5$ is H, then —$N(R^e)_2$ is not selected from the group consisting of N-(2-methoxyethyl)amino, cycloheptylamino, N-(aminocarbonyl)amino, N-(2-methoxyethyl)-N-methylamino, cyclopropylamino, isopropylamino, propylamino, N-(ethyl)-N-methylamino, ethylamino, methylamino, N-(acetyl)amino, N,N-diisopropylamino, N,N-diethylamino, and N-(isopropyl)-N-methylamino; and provided that when $R^1$ is H, $R^3$ is H, X is N(H), $R^4$ is H, $R^6$ is H and $R^5$ is H, then —N($R^e$)$_2$ is not selected from the group consisting of aminocarbonylamino, N-(2-hydroxypropyl)amino, cycloheptylamino, N-(2-methoxyethyl)amino, N-(2-methoxyethyl)-N-methylamino, cyclopropylamino, methylamino, ethylamino, isopropylamino, N-(ethyl)-N-methylamino, N-(isopropyl)-N-methylamino, propylamino, N,N-diisopropylamino, N-(acetyl)amino, N,N-diethylamino and N,N-dimethylamino; and provided that when $R^1$ is H, $R^3$ is H, X is N(H), $R^5$ is H, $R^6$ is H and each $R^e$ is H; then $R^4$ is not selected from the group consisting of H, cyclohexyl, butyl, phenyl, cyclopropyl, benzyl, isopropyl, propyl, isobutyl, ethyl, and methyl; and provided that when $R^1$ is H, $R^3$ is H, X is N(H), $R^5$ is H, $R^6$ is H and each $R^e$ is $CH_3$; then $R^4$ is not selected from the group consisting of methyl, isopropyl, and isobutyl; and provided that when $R^1$ is H, $R^3$ is H, X is N($R^a$), $R^4$ is H, $R^5$ is H, $R^6$ is H and each $R^e$ is H; then $R^a$ is not selected from the group consisting of cyclobutyl, 2-methoxyethyl, cyclohexyl, cyclopentyl, propyl, cyclopropyl, butyl, isopropyl, 3-pentyl, benzyl, ethyl, and methyl; and provided the compound of formula (I) is not selected from the group consisting of:

1,2,4-Triazine-3,5(2H,4H)-dione, 6-[(2-amino-1-cyclopropylethyl)methylamino];
1,2,4-Triazine-3,5(2H,4H)-dione, 6-[(2-amino-1-methylethyl)methylamino]-2,4-dimethyl;
1,2,4-Triazine-3,5(2H,4H)-dione, 6-[(2-amino-1-methylethyl)methylamino];
1,2,4-Triazine-3,5(2H,4H)-dione, 6-[(2-amino-3-methoxypropyl)methylamino];
1,2,4-Triazine-3,5(2H,4H)-dione, 2,4-dimethyl-6-[methyl[2-(methylamino)ethyl]amino];
1,2,4-Triazine-3,5(2H,4H)-dione, 6-[(2-aminopropyl)methylamino]-2,4-dimethyl-;
1,2,4-Triazine-3,5(2H,4H)-dione, 6-[(2-aminopropyl)methylamino]-;
1,2,4-Triazine-3,5(2H,4H)-dione, 6-[methyl[2-(methylamino)ethyl]amino]-;
1,2,4-Triazine-3,5(2H,4H)-dione, 6-[[2-(diethylamino)ethyl]amino]-2,4-di-2-propen-1-yl-;
1,2,4-Triazine-3,5(2H,4H)-dione, 6-[[2-(diethylamino)ethyl]amino]-2,4-dipropyl-;
1,2,4-Triazine-3,5(2H,4H)-dione, 6-[[2-(diethylamino)ethyl]amino]-2,4-bis(2-methyl-2-propen-1-yl)-;
1,2,4-Triazine-3,5(2H,4H)-dione, 6-[[2-(diethylamino)ethyl]amino]-2,4-bis-(2-methoxyethyl)-;
1,2,4-Triazine-3,5(2H,4H)-dione, 6-[[2-(diethylamino)ethyl]amino]-2,4-bis(1-methylethyl)-;
1,2,4-Triazine-3,5(2H,4H)-dione, 6-[[2-(diethylamino)-1-methylethyl]amino]-2,4-dimethyl-;
1,2,4-Triazine-3,5(2H,4H)-dione, 6-[[2-(diethylamino)-1-methylethyl]amino]-;
1,2,4-Triazine-3,5(2H,4H)-dione, 6-[[2-(diethylamino)ethyl]amino]-2,4-diethyl-;
1,2,4-Triazine-3,5(2H,4H)-dione, 6-[(2-amino-3-methoxypropyl)methylamino]-2,4-dimethyl-;
1,2,4-Triazine-3,5(2H,4H)-dione, 6-[[(1R,2R)-2-aminocyclohexyl]amino]-;
1,2,4-Triazine-3,5(2H,4H)-dione, 6-[(2-aminocycloheptyl)amino]-2,4-dimethyl-;
1,2,4-Triazine-3,5(2H,4H)-dione, 6-[(2-aminocyclopentyl)amino]-2,4-dimethyl-;
1,2,4-Triazine-3,5(2H,4H)-dione, 6-[(2-aminocycloheptyl)amino]-;
1,2,4-Triazine-3,5(2H,4H)-dione, 6-[(2-aminocyclohexyl)amino]-;
1,2,4-Triazine-3,5(2H,4H)-dione, 6-[(2-aminocyclohexyl)amino]-2,4-dimethyl-;
1,2,4-Triazine-3,5(2H,4H)-dione, 6-[(2-amino-2-ethylbutyl)amino]-;
1,2,4-Triazine-3,5(2H,4H)-dione, 6-[(2-amino-2-ethylbutyl)amino]-2,4-dimethyl-;
1,2,4-Triazine-3,5(2H,4H)-dione, 6-[(2-amino-2-methylpropyl)amino]-2,4-dimethyl-;
1,2,4-Triazine-3,5(2H,4H)-dione, 6-[(2-amino-2-methylpropyl)amino]-;
1,2,4-Triazine-3,5(2H,4H)-dione, 6-[[2-(dimethylamino)-2-methylpropyl]amino]-2,4-dimethyl-;
1,2,4-Triazine-3,5(2H,4H)-dione, 6-[[2-(dimethylamino)-2-methylpropyl]amino]-;
1,2,4-Triazine-3,5(2H,4H)-dione, 6-[(2-amino-2,3-dihydro-1H-inden-1-yl)amino]-2,4-dimethyl-;
1,2,4-Triazine-3,5(2H,4H)-dione, 6-[(2-amino-2,3-dihydro-1H-inden-1-yl)amino]-;
1,2,4-Triazine-3,5(2H,4H)-dione, 6-[(2-aminocyclopentyl)amino]-; and
1,2,4-Triazine-3,5(2H,4H)-dione, 6,6'-(1,2-ethanediyldiimino)bis-.

In certain embodiments $R^1$ is methyl or ethyl.
In certain embodiments $R^1$ is methyl.
In certain embodiments $R^6$ is H or methyl.
In certain embodiments $R^6$ is H.
In certain embodiments $R^6$ is methyl.
In certain embodiments the group:

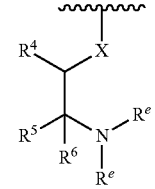

is selected from the group consisting of:

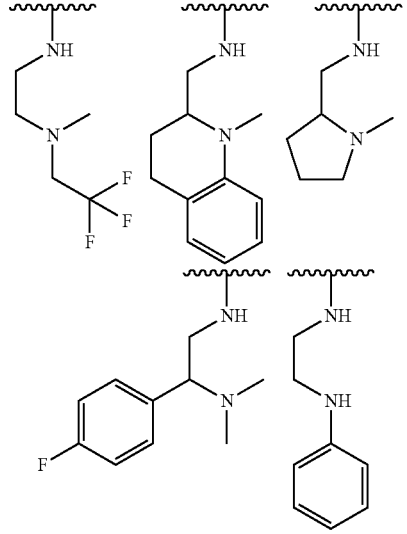

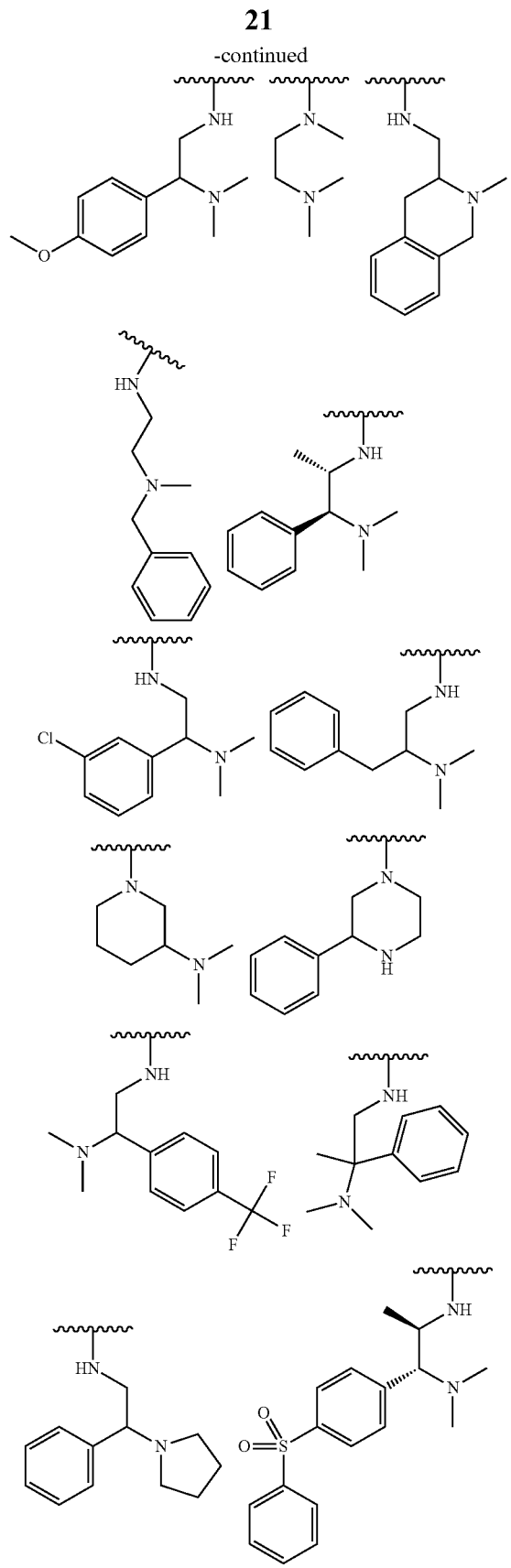

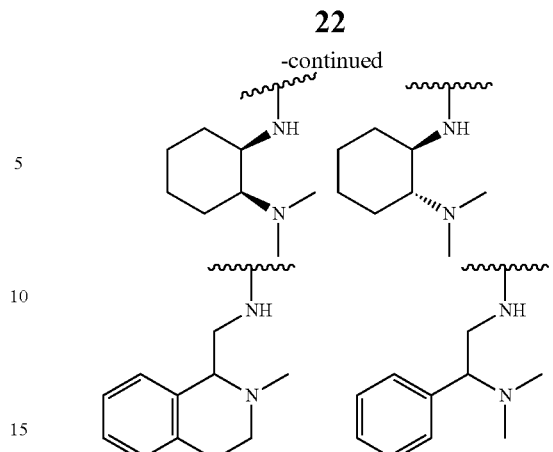

and

In certain embodiments the group:

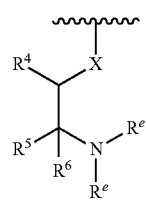

is selected from the group consisting of:

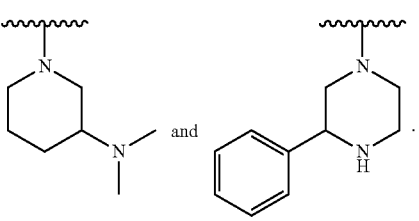

In certain embodiments $R^3$ is methyl or ethyl.
In certain embodiments $R^3$ is methyl.
In certain embodiments $R^4$ is hydrogen or methyl.
In certain embodiments $R^5$ is selected from the group consisting of H, 4-fluorophenyl, 4-methoxyphenyl, 3-chlorophenyl, benzyl, 4-(trifluoromethyl)phenyl, phenyl, and 4-(phenylsulfonyl)phenyl.
In certain embodiments $R^4$ and $R^5$ taken together with the atoms to which they are attached form a carbocyclyl or heterocyclyl, which carbocyclyl and heterocyclyl is optionally substituted with one or more groups $R^c$.
In certain embodiments $R^4$ and $R^5$ taken together with the atoms to which they are attached form a cyclohexane, which is optionally substituted with one or more groups $R^c$.
In certain embodiments $R^a$ and one $R^e$ taken together with the atoms to which they are attached form a 5-membered or 6-membered heterocyclyl, which 5-membered and 6-membered heterocyclyl is optionally substituted with one or more groups $R^b$.
In certain embodiments $R^a$ and one $R^e$ taken together with the atoms to which they are attached form a 6-membered heterocyclyl.
In certain embodiments $R^a$ and $R^4$ taken together with the atoms to which they are attached form a 5-membered or 6-membered heterocyclyl, which 5-membered and 6-membered heterocyclyl is optionally substituted with one or more groups $R^b$.

In certain embodiments $R^a$ and $R^4$ taken together with the atoms to which they are attached form a 6-membered heterocyclyl.

In certain embodiments $R^a$ and $R^5$ taken together with the atoms to which they are attached form a 5-membered or 6-membered heterocyclyl, which 5-membered and 6-membered heterocyclyl is optionally substituted with one or more groups $R^b$.

In certain embodiments $R^e$ taken together with $R^5$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from oxo, halo, amino, hydroxy, $C_{1-6}$alkoxy and carbocyclyl.

In certain embodiments $R^e$ taken together with $R^5$ and the atoms to which they are attached form a heterocyclyl that is optionally substituted with one or more groups independently selected from the group consisting of $C_{1-6}$alkyl.

In certain embodiments two $R^e$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo.

In certain embodiments one $R^e$ taken together with $R^4$ and the atoms to which they are attached form a heterocyclyl that is optionally substituted with one or more groups independently selected from the group consisting of $C_{1-6}$alkyl, $C_{2-6}$alkenyl, $C_{2-6}$alkynyl, and $C_{1-6}$alkoxy, wherein each $C_{1-6}$alkyl, $C_{2-6}$alkenyl, $C_{2-6}$alkynyl, and $C_{1-6}$alkoxy is optionally substituted with one or more groups independently selected from the group consisting of oxo, halo, amino, hydroxy, $C_{1-6}$alkoxy and carbocyclyl.

In certain embodiments the compound is selected from the group consisting of:

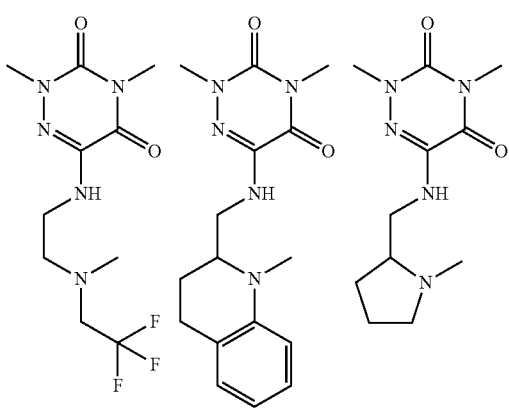

-continued

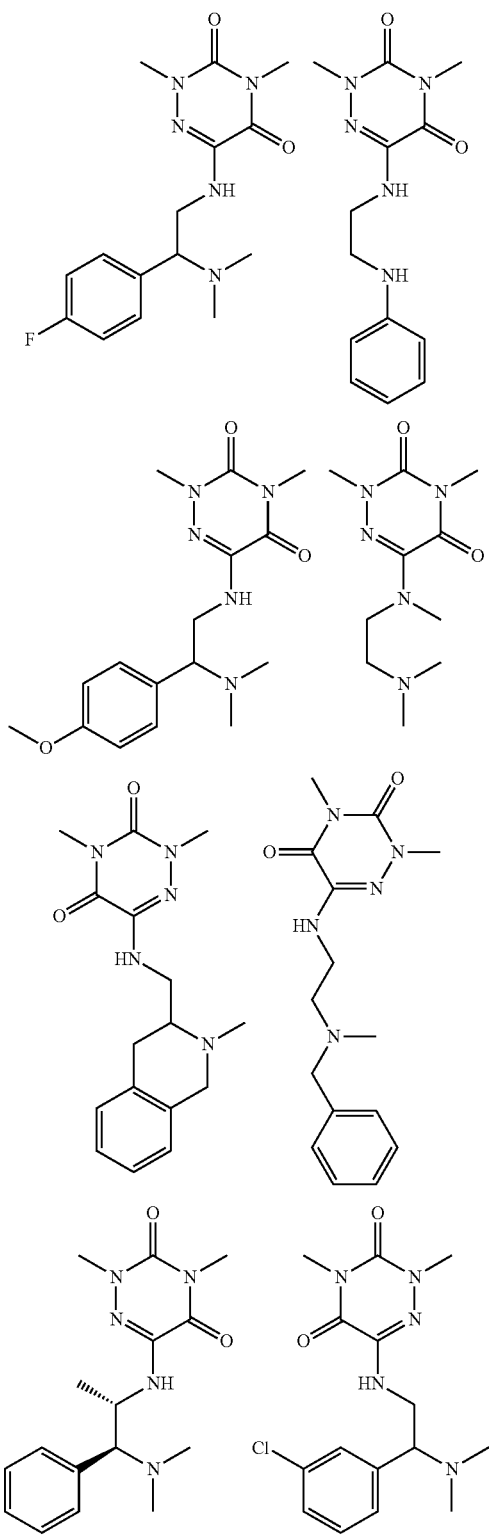

-continued

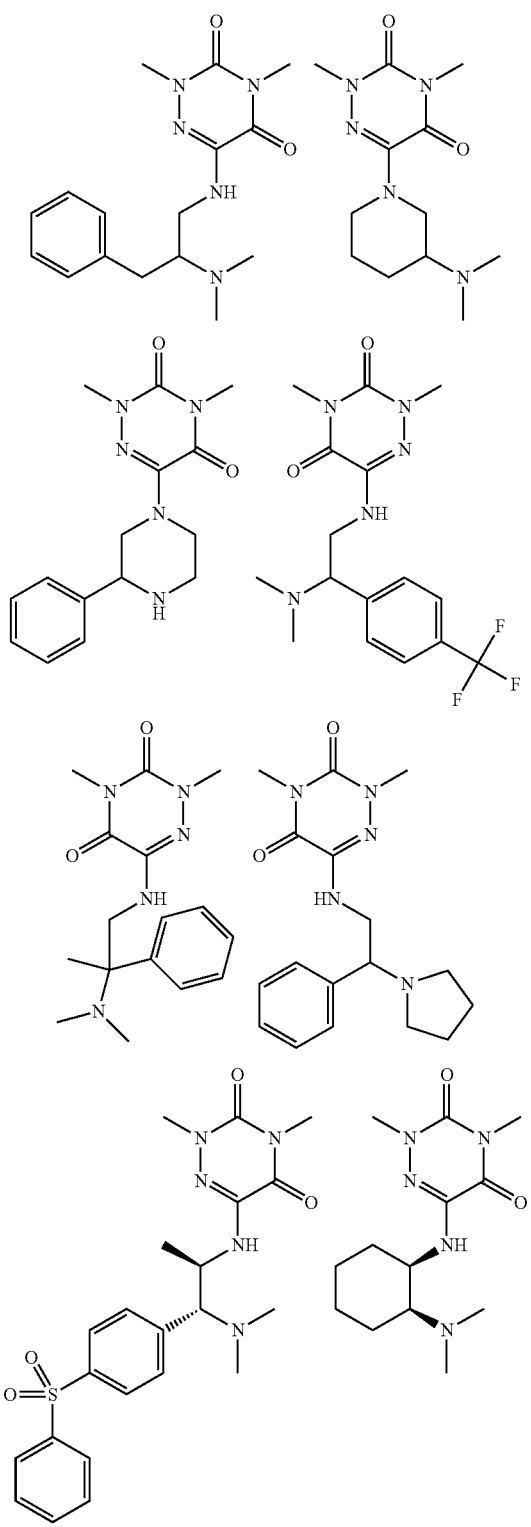

-continued

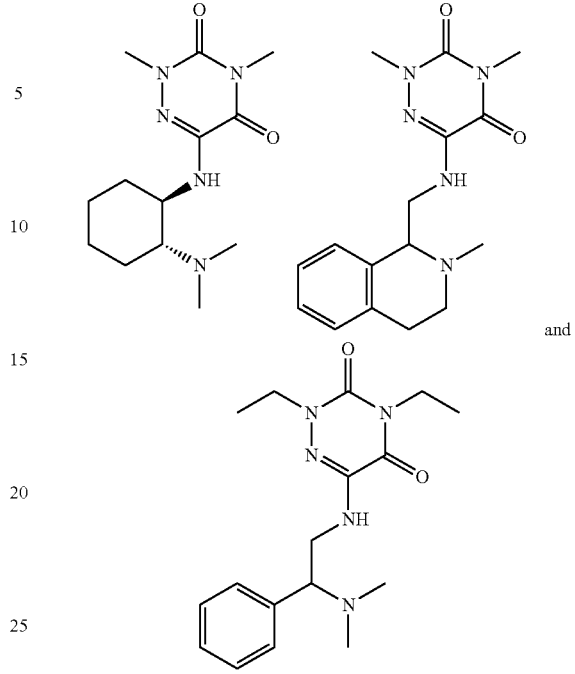

and salts thereof.

In certain embodiments R¹ is selected from the group consisting of $C_{1-6}$alkyl, $C_{2-6}$alkenyl, $C_{2-6}$alkynyl, carbocyclyl, and heterocyclyl, wherein each $C_{1-6}$alkyl, $C_{2-6}$alkenyl, $C_{2-6}$alkynyl, carbocyclyl, and heterocyclyl is optionally substituted with one or more groups independently selected from the group consisting of oxo, halo, amino, hydroxy, and $C_{1-6}$alkoxy.

In certain embodiments the compound of Formula (I) is a compound as described in the Examples herein, or a freebase or salt thereof.

Uses, Formulation and Administration

Pharmaceutically Acceptable Compositions

Another aspect includes a pharmaceutical composition comprising a compound of formula (I) or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit a bromodomain of PCAF. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula I or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula I or salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula I or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound of formula (I) or salt thereof, and optionally, further comprises one or more excipients.

In another embodiment, compositions comprise liquid dosage formulations comprising a compound of formula I or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I).

Example dosage forms for topical or transdermal administration of a compound of formula (I) include ointments, pastes, creams, lotions, gels, powders, solutions, sprays, inhalants or patches. The compound of formula (I) or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula I or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula I or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or a salt thereof for the inhibition of a bromodomain of PCAF (in vitro or in vivo).

Another embodiment includes a method for treating a PCAF mediated disorder in an animal (e.g., a mammal such as a human) comprising administering a compound of formula (I), or a pharmaceutically acceptable salt thereof to the animal. PCAF mediated disorders include, but are not limited to those disorders described herein.

Another aspect includes the use of a compound of formula (I) or a salt thereof for the inhibition of a bromodomain of GCN5 (in vitro or in vivo).

Another embodiment includes a method for treating a GCN5 mediated disorder in an animal (e.g., a mammal such as a human) comprising administering a compound of formula (I), or a pharmaceutically acceptable salt thereof to the animal.

Another embodiment includes a method of increasing efficacy of a cancer treatment comprising a cytotoxic agent in an animal (e.g., a mammal such as a human) comprising administering to the animal an effective amount of a compound of formula (I) or a pharmaceutically acceptable salt thereof.

Another embodiment includes a method of delaying or preventing development of cancer resistance to a cytotoxic agent in an animal (e.g., a mammal such as a human), comprising administering to the animal a compound of formula (I) or a pharmaceutically acceptable salt thereof.

Another embodiment includes a method of extending the duration of response to a cancer therapy in an animal (e.g., a mammal such as a human), comprising administering to an animal undergoing the cancer therapy a compound of formula (I) or a pharmaceutically acceptable salt thereof, wherein the duration of response to the cancer therapy when the compound of formula (I) or the pharmaceutically acceptable salt thereof is administered is extended over the duration of response to the cancer therapy in the absence of the administration of the compound of formula (I) or the pharmaceutically acceptable salt thereof.

Another embodiment includes a method of treating cancer in an individual comprising administering to the individual (a) a compound of formula (I) or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

PCAF Mediated Disorders

A "PCAF mediated disorder" is characterized by the participation of PCAF in the inception, manifestation of one or more symptoms or disease markers, severity, or progression of a disorder.

PCAF mediated disorders include cancers, including, but not limited to acoustic neuroma, acute leukemia, acute lymphocytic leukemia, acute myelocytic leukemia, acute T-cell leukemia, androgen-responsive prostate cancer, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, drug resistant breast cancer, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastric cancer, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pediatric acute lymphoblastic leukemia, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, wnt-dependent breast cancer, testicular tumors, uterine cancer, and Wilms' tumor.

In certain embodiments, the cancer is selected from the group consisting of gastric cancer, lung cancer, non-small cell lung cancer, pancreatic cancer, pediatric acute lymphoblastic leukemia, androgen-responsive prostate cancer, breast cancer, wnt-dependent breast cancer, drug-resistant breast cancer, estrogen-receptor positive breast cancer, leukemia, neuroblastoma, colon cancer, and cervical cancer. In certain embodiments, the cancer is lung cancer. In certain embodiments, the cancer is pancreatic cancer. In certain embodiments, the cancer is breast cancer. In certain embodiments, the cancer is leukemia. In certain embodiments, the cancer is colon cancer. In certain embodiments, the cancer is cervical cancer.

PCAF mediated disorders also include inflammatory diseases, inflammatory conditions, and autoimmune diseases, including, but not limited to: Addison's disease, acute gout, Alzheimer's disease (inflammatory-mediated neurotoxicity), ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In some embodiments, the disorder is an autoimmune disease. In some embodiments, the disorder is asthma.

PCAF mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radiocontrast agent induced, sepsis induced, pneumonia induced, and drug toxicity induced; HIV infection; obesity; osteoporosis, dyslipidemia; hypercholesterolemia; Alzheimer's disease; metabolic syndrome; hepatic steatosis; type II diabetes; insulin resistance; diabetic retinopathy; osteoporosis; obesity, and parasitic infection (e.g., Toxoplasma gondii). In some embodiments, the disorder is osteoporosis. In some embodiments, the disosrder is obesity. In some embodiments, the disorder is HIV infection. In some embodiments, the disorder is parasitic infection.

GCN5 Mediated Disorders

A "GCN5 mediated disorder" is characterized by the participation of the GCN5 in the inception, manifestation of one or more symptoms or disease markers, severity, or progression of a disorder.

GCN5 mediated disorders include cancers, including, but not limited to acoustic neuroma, acute leukemia, acute lymphocytic leukemia, acute myelocytic leukemia, acute T-cell leukemia, androgen-responsive prostate cancer, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, drug resistant breast cancer, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, gastric cancer, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pediatric acute lymphoblastic leukemia, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, wnt-dependent breast cancer, testicular tumors, uterine cancer, and Wilms' tumor.

In certain embodiments, the cancer is selected from the group consisting of gastric cancer, lung cancer, non-small cell lung cancer, pancreatic cancer, pediatric acute lymphoblastic leukemia, androgen-responsive prostate cancer, breast cancer, wnt-dependent breast cancer, drug-resistant breast cancer, estrogen-receptor positive breast cancer, leukemia, neuroblastoma, colon cancer, and cervical cancer. In certain embodiments, the cancer is lung cancer. In certain embodiments, the cancer is pancreatic cancer. In certain embodiments, the cancer is breast cancer. In certain embodiments, the cancer is leukemia. In certain embodiments, the cancer is colon cancer. In certain embodiments, the cancer is cervical cancer.

GCN5 mediated disorders also include inflammatory diseases, inflammatory conditions, and autoimmune diseases, including, but not limited to: Addison's disease, acute gout, Alzheimer's disease (inflammatory-mediated neurotoxicity), ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In some embodiments, the disorder is an autoimmune disease. In some embodiments, the disorder is asthma.

GCN5 mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radiocontrast agent induced, sepsis induced, pneumonia induced, and drug toxicity induced; HIV infection; obesity; osteoporosis, dyslipidemia; hypercholesterolemia; Alzheimer's disease; metabolic syndrome; hepatic steatosis; type II diabetes; insulin resistance; diabetic retinopathy; osteoporosis; obesity, and parasitic infection (e.g., Toxoplasma gondii). In some embodiments, the disorder is osteoporosis. In some embodiments, the disosrder is obesity. In some embodiments, the disorder is HIV infection. In some embodiments, the disorder is parasitic infection.

Co-Administration of Compounds and Other Agents

The compounds of formula (I) or salts thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (I) or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors, and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®., Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO098/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos: 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugswith analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

For treating an inflammatory disease or an autoimmune disease, a compound of formula (I) or a pharmaceutically acceptable salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RII, siL-6R), an antiinflammatory cytokine (e.g. IL-4, IL-10, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCVacetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCI0-469, VX-702, AMG-548, VX-740, Roflumilast, IC-485, CDC-801, S1P1 agonists (such as FTY720), a PKC family inhibitor (e.g. Ruboxistaurin or AEB-071) or Mesopram. In certain embodiments, a compound of formula (I) or a pharmaceutically acceptable salt thereof may be co-administered with methotrexate or leflunomide. In moderate or severe Rheumatoid arthritis cases, a compound of formula (I) or a pharmaceutically acceptable salt thereof may be co-administered with cyclosporine and anti-TNF antibodies as noted above. A compound of formula (I) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), and an antiinflammatory cytokine (e.g. IL-4, IL-10, IL-11, IL-13 or TGF).

For treating Crohn's disease, a compound of formula (I) or a pharmaceutically acceptable salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of formula (I) or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-1ra); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula (I) or a pharmaceutically acceptable salt thereof may be co-administered with a corticosteroid; prednisolone; methylprednisolone; azathioprine; cyclophosphamide; cyclosporine; methotrexate; 4-aminopyridine; tizanidine; interferon-1a (AVONEX®; Biogen); interferon-1b (BETASERON®; Chiron/Berlex); interferon-n3) (Interferon Sciences/Fujimoto), interferon-(Alfa Wassermann/J&J), interferon 1A-IF (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g. TNF, LT, IL-1, IL-2, IL-6, IL-7, IL-8, IL-12, IL-23, IL-15, IL-16, EMAP-II, GM-CSF, FGF, or PDGF).

For treating AIDS a compound of formula (I) or a pharmaceutically acceptable salt thereof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) or a pharmaceutically acceptable salt thereof may also be co-administered with methotrexate, cyclosporine, FK506, rapamycin, mycophenolate mofetil, leflunomide, an S1P1 agonist, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a TACE inhibitor, a T-cell signaling inhibitor (e.g. a kinase inhibitor), a metalloproteinase inhibitor, sulfasalazine, azathioprine, a 6-mercaptopurine, an angiotensin converting enzyme inhibitor, a soluble cytokine receptor (e.g. soluble p55 or p75 TNF receptors, siL-1RI, siL-1RII, or siL-6R), or an antiinflammatory cytokine (e.g. IL-4, IL-1 0, IL-13 or TGF).

A compound of formula (I) or a pharmaceutically acceptable salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNS03, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, a n anti-IL-6 receptor antibody, neurovax, pirfenidone allotrap 1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula (I) or a pharmaceutically acceptable salt thereof may be co-administered with ibuprofen, diclofenac, misoprostol, naproxen, meloxicam, indometacin, diclofenac, celecoxib, rofecoxib, sulfasalazine, methotrexate, azathioprine, minocyclin, prednisone, a n anti-TNF antibody, D2E7 (HUMIRA®), CA2 (infliximab), CDP 571, a TNFR-Ig construct, (p75TNFRigG (ENBREL®), or p55TNFRigG (LENERCEPT®).

For treating asthma a compound of formula (I) or a pharmaceutically acceptable salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of formula (I) or a pharmaceutically acceptable salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of formula (I) or a pharmaceutically acceptable salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of formula (I) or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula (I) or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); an inhibitor ofPDE4, or a purine synthesis inhibitor (e.g. Cellcept®). For example, a compound of formula (I) or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-1), or a caspase inhibitor (e.g. a IL-1 converting enzyme inhibitor or IL-1ra).

A compound of formula (I) or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula (I) or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula (I) or a pharmaceutically acceptable salt thereof can also be co-administered with LJP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERCEPT™).

A compound of formula (I) or a pharmaceutically acceptable salt thereof can also be co-administered with one or more agents used in the prevention or treatment of AIDS: an HIV reverse transcriptase inhibitor, an HIV protease inhibitor, an immunomodulator, or another retroviral drug. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

For treating type II diabetes, hepatic steatosis, insulin resistance, metabolic syndrome or a related disorder, a compound of formula (I) or a pharmaceutically acceptable salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide or tolbutamide; agents that are glucagon-like peptide agonists such as exanatide, liraglutide or taspoglutide; agents that inhibit dipeptidyl-peptidase IV such as vildagliptin, sitagliptin, saxagliptin, linagliptin, allogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders or a chronic kidney disease, a compound of formula (I) or a pharmaceutically acceptable salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

The amount of both the compound of formula (I) or salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 μg/kg body weight/day of the additional therapeutic agent can be administered.

Provided herein are methods of extending the duration of response to a cytotoxic agent in an individual with cancer comprising administering to the individual (a) an effective amount of a compound of formula (I) or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl) ethylamino)methyl)furan-2-yl)quinazolin-4-amine,di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

EXEMPLIFICATION

Experimental Procedure for Intermediate A

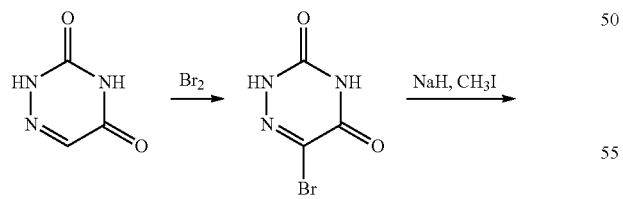

Intermediate A

Step 1

6-bromo-1,2,4-triazine-3,5(2H,4H)-dione

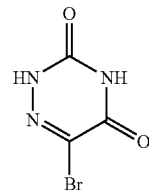

Br$_2$ (20.3 mL, 406.8 mmol) was added to a stirred solution of 1,2,4-triazine-3,5(2H,4H)-dione (20 g, 176.8 mmol) in water (250 mL) at ambient temperature. After addition, the mixture was stirred at 25° C. for 12 h, at which time TLC indicated the reaction had gone to completion. The resulting solid was collected by filtration washed with water, and dried under reduced pressure to give the title compound (15.0 g, 44% yield) as a white solid. LCMS M/Z (M+H) 191, 193.

Step 2

6-bromo-2,4-dimethyl-1,2,4-triazine-3,5(2H,4H)-dione

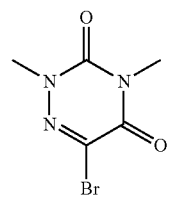

Sodium hydride (60%, 2.6 g, 65.1 mmol) was slowly added to a stirred and cooled solution of 6-bromo-2,4-dimethyl-1,2,4-triazine-3,5(2H,4H)-dione (5.0 g, 26.0 mmol) in DMF (100 mL). After addition, the mixture was stirred at 0° C. for 1 h, and then iodomethane (9.2 g, 65.1 mmol) was added dropwise and the resulting mixture was stirred at ambient temperature for 2 h. The reaction was quenched by addition of saturated aqueous ammonium chloride (100 mL), and then extracted with ethyl acetate (3×100 mL). The combined organic extracts were dried over Na$_2$SO$_4$ and concentrated in vacuo to give the title compound (3.5 g, 61% yield) as a red solid. This crude material was used in the next step without further purification. LCMS M/Z (M+H) 219, 221.

Experimental Procedure for Intermediate B

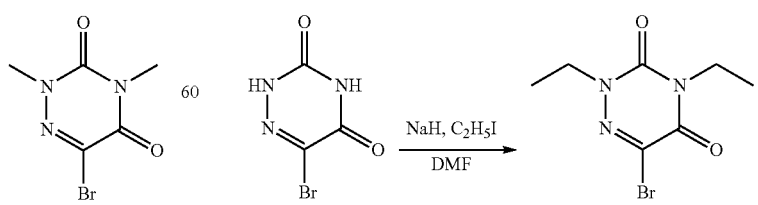

Intermediate B

Step 1

6-bromo-2,4-diethyl-1,2,4-triazine-3,5(2H,4H)-dione

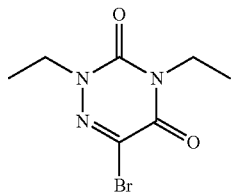

Sodium hydride (60%, 2.6 g, 65.1 mmol) was slowly added to a stirred and cooled (0° C.) solution of 6-bromo-2,4-dimethyl-1,2,4-triazine-3,5(2H,4H)-dione (5.0 g, 26.0 mmol) in DMF (100 mL). After addition, the mixture was stirred at 0° C. for 1 h, and then iodoethane (10.2 g, 65.1 mmol) was added dropwise and the resulting mixture was stirred at ambient temperature for 2 h. The reaction was quenched by addition of saturated aqueous ammonium chloride (100 mL), and then extracted with ethyl acetate (3×100 mL). The combined organic extracts were dried over Na$_2$SO$_4$ and concentrated under reduced pressure to give the title compound (3.8 g, 59% yield) as a red solid. This crude material was used in the next step without further purification. LCMS M/Z (M+H) 248, 250.

Experimental Procedure for Intermediate C

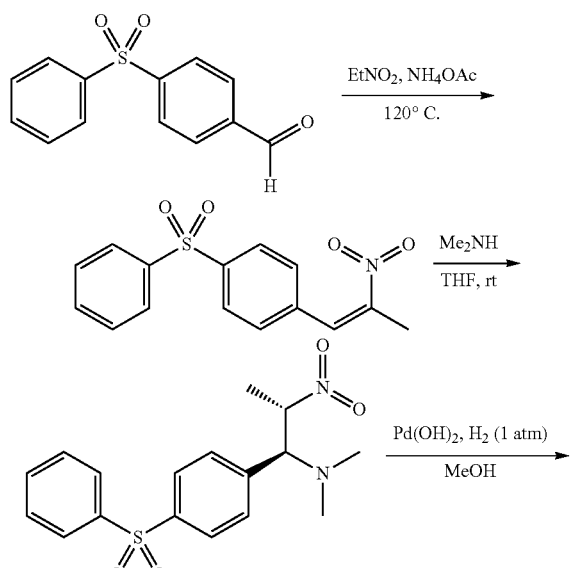

Intermediate C

Step 1

1-(2-nitroprop-1-en-1-yl)-4-(phenylsulfonyl)benzene

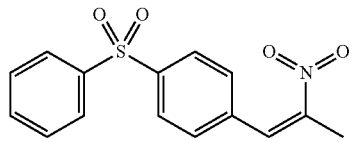 [SMILES: C/C(=C/c1ccc(S(=O)(=O)c2ccccc2)cc1)[N+](=O)[O-]]

A mixture of 4-(phenylsulfonyl)benzaldehyde (1.00 g, 4.06 mmol), nitroethane (3.05 g, 40.6 mmol) and ammonium acetate (0.08 g, 1.01 mmol) was heated at 120° C. for 2 h. The resulting mixture was cooled, concentrated in vacuo and purified on a 40 g biotage column with hexane to 30% ethyl acetate in hexane to provide the title compound (360 mg, 30% yield). LCMS M/Z (M+Na) 326. The E/Z stereochemistry or ratio was not determined.

Step 2

(1S,2S)—N,N-dimethyl-2-nitro-1-(4-(phenylsulfonyl)phenyl)propan-1-amine

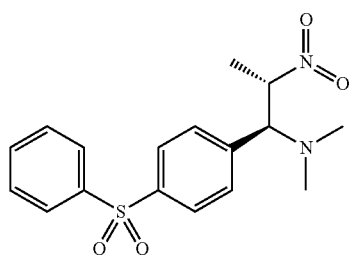 [SMILES: C[C@@H]([C@H](c1ccc(S(=O)(=O)c2ccccc2)cc1)N(C)C)[N+](=O)[O-]]

To 1-(2-nitroprop-1-en-1-yl)-4-(phenylsulfonyl)benzene (0.36 g, 1.19 mmol) was added a 2M dimethylamine solution in THF (0.72 mL, 1.43 mmol). After completion of the reaction the reaction mixture was concentrated in vacuo and co-evaporated with methanol to provide the title compound as a white solid (360 mg, 87% yield), an unstable compound that is immediately used in the next step. LCMS M/Z (M+H) 349. The compound was isolated as a racemic mixture with unknown relative stereochemistry: the assignment was based on the most probable according to the literature.

Step 3

(1S,2S)—N1,N1-dimethyl-1-(4-(phenylsulfonyl)phenyl)propane-1,2-diamine

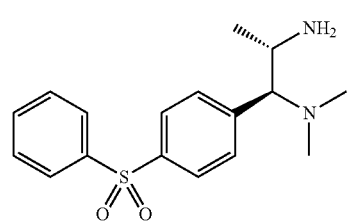 [SMILES: C[C@H](N)[C@H](c1ccc(S(=O)(=O)c2ccccc2)cc1)N(C)C]

To (1S,2S)—N,N-dimethyl-2-nitro-1-(4-(phenylsulfonyl) phenyl)propan-1-amine (0.36 g, 1.03 mmol) in methanol (10 mL) was added palladium hydroxide (0.14 g, 1.03 mmol). The resulting mixture was stirred under 1 atmosphere of hydrogen for 18 h. The mixture was filtered over celite and the filtrate was concentrated in vacuo to dryness. The residue was used as such in the next step. LCMS M/Z (M+H) 319. The compound was isolated as a racemic mixture with unknown relative stereochemistry: the assignment was based on the previous step.

Experimental Procedure for Intermediate D (1S,2S)—N1,N1-dimethyl-1-phenylpropane-1,2-diamine

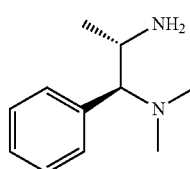

The title intermediate was prepared in a similar fashion to Intermediate C. LCMS M/Z (M+H) 179. The compound was isolated as a racemic mixture with unknown relative stereochemistry (E/Z stereochemistry not determined at Step 1): the assignment was based on the most probable according to the literature.

Experimental Procedure for Intermediate E

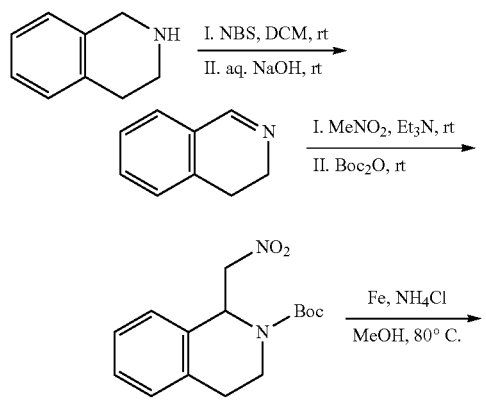

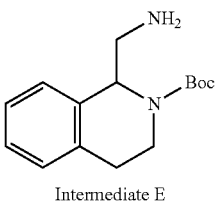

Intermediate E

Step 1

3,4-dihydroisoquinoline

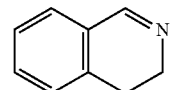

To a stirred solution of 1,2,3,4-tetrahydroisoquinoline (5.0 g, 37.54 mmol) in DCM (200 mL) was added NBS (7.4 g, 41.3 mmol) in portions over 20 min. After addition, the mixture was stirred at ambient temperature for 1 h. Aqueous NaOH (wt 30%, 50 mL) was added and stirring was continued for another 1 h. The separated organic layer was washed with water, dried over $Na_2SO_4$ and concentrated under reduced pressure to give the crude title compound (3.8 g, 77% yield) as a brown oil. LCMS M/Z (M+H) 132.

Step 2 tert-butyl 1-(nitromethyl)-3,4-dihydroisoquinoline-2(1H)-carboxylate

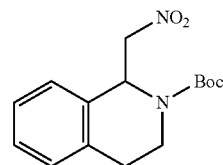

To a solution of 3,4-dihydroisoquinoline (2.0 g, 15.2 mmol) in $MeNO_2$ (25 mL) was added $Et_3N$ (1.7 g, 16.8 mmol). The mixture was stirred at ambient temperature for 5 h. Then, $Boc_2O$ (6.6 g, 30.4 mmol) was added and the resulting mixture was stirred at ambient temperature for another 10 h. The mixture was diluted with ethyl acetate (50 mL) and washed with water (3×30 mL). The separated organic layer was dried over $Na_2SO_4$ and concentrated under reduced pressure. The crude product was purified by silica gel chromatography (petroleum ether:ethyl acetate=9:1) to give the crude title compound (3.5 g, 80% yield) as a white solid. LCMS M/Z (M+H) 293.

Step 3 tert-butyl 1-(aminomethyl)-3,4-dihydroisoquinoline-2(1H)-carboxylate

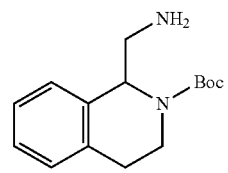 [SMILES: CC(C)(C)OC(=O)N1CCc2ccccc2C1CN]

To a solution of tert-butyl 1-(nitromethyl)-3,4-dihydroisoquinoline-2(1H)-carboxylate (1.0 g, 3.24 mmol) in MeOH (25 mL) and $H_2O$ (15 mL) was added iron (0.960 g, 17.1 mmol) and NH₄Cl (0.91 g, 17.1 mmol). The resulting suspension was heated at 80° C. for 2 h, at which time LCMS indicated the reaction had reached completion. After the reaction was cooled, the solid was removed by filtration. The filtrate was diluted with ethyl acetate (80 mL) and washed with water (2×50 mL). The separated organic layer was dried over Na₂SO₄ and concentrated under reduced pressure to give the crude title compound (600 mg, 67% yield). This crude was pure enough to be used in next step without purification. LCMS M/Z (M+H) 263. The compound was isolated as a racemic mixture.

Example 1

2,4-dimethyl-6-((2-(methyl(2,2,2-trifluoroethyl)amino)ethyl)amino)-1,2,4-triazine-3,5(2H,4H)-dione

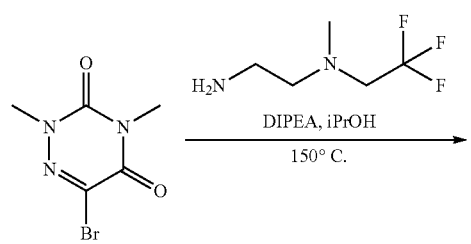

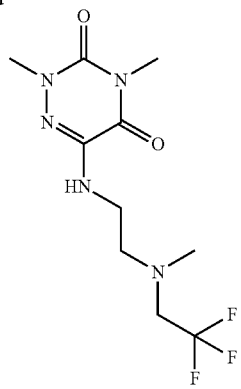

Example 1

A mixture of 6-bromo-2,4-dimethyl-1,2,4-triazine-3,5 (2H,4H)-dione (Intermediate A, 200 mg, 0.91 mmol), N¹-methyl-N¹-(2,2,2-trifluoroethyl)ethane-1,2-diamine (426 mg, 2.73 mmol) and DIPEA (587 mg, 4.54 mmol) in isopropanol (3 mL) was heated at 150° C. in the microwave condition for 2 h under an atmosphere of N₂, at which time LCMS indicated the reaction had gone to completion. The mixture was concentrated under reduced pressure and the residue was purified by reverse phase chromatography (acetonitrile 7-37%/0.1% NH₄OH in water) to give the title compound (7.0 mg, 3%) as a white solid. ¹H NMR (400 MHz, CDCl₃) δ 5.62 (s, 1H), 3.51 (s, 3H), 3.38 (s, 3H), 3.31-3.27 (m, 2H), 3.09-3.05 (m, 2H), 2.84-2.81 (m, 2H), 2.48 (s, 3H). LCMS M/Z (M+H) 296.

Examples 2-3

The following compounds were prepared in a similar fashion to Example 1. All examples in the following table were prepared using commercially available amines.

| Example | Compound Name | NMR | M/Z (M + H) |
|---|---|---|---|
| 2 | 2,4-dimethyl-6-(((1-methyl-1,2,3,4-tetrahydroquinolin-2-yl)methyl)amino)-1,2,4-triazine-3,5(2H,4H)-dione | ¹H NMR (400 MHz, Methanol-d4) δ 7.04-7.00 (m, 1H), 6.94-6.90 (m, 1H), 6.57-6.52 (m, 2H), 3.64-3.58 (m, 2H), 3.50-3.45 (s, 3H), 3.33-3.26 (s, 3H), 3.24 (s, 3H), 2.95-2.85 (m, 1H), 2.65-2.61 (m, 1H), 2.44-2.00 (m, 1H), 1.85-1.74 (m, 2H). (Racemic mixture) | 316 |

| Example | Compound Name | NMR | M/Z (M + H) |
|---|---|---|---|
| 3 | 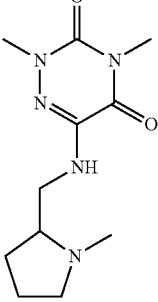<br>2,4-dimethyl-6-(((1-methylpyrrolidin-2-yl)methyl)amino)-1,2,4-triazine-3,5(2H,4H)-dione | ¹H NMR (400 MHz, DMSO-d6) δ 6.19-6.32 (m, 1H), 3.36 (s, 3H), 3.33 (br. s., 1H), 3.26 (ddd, J = 3.07, 6.84, 13.30 Hz, 1H), 3.16-3.19 (m, 3H), 2.94-3.06 (m, 2H), 2.45 (d, J = 5.04 Hz, 1H), 2.25-2.30 (m, 3H), 2.11-2.20 (m, 1H), 1.78-1.89 (m, 1H), 1.49-1.67 (m, 3H). (Racemic mixture) | 254 |

Examples 4-17

The following compounds were prepared in a similar fashion to Example 1, using n-butanol at 180° C. instead of isopropanol at 150° C. For the Example 17 the Intermediate D was used as reactant. All other examples in the following table were prepared using commercially available amines.

| Example | Compound Name | NMR | M/Z (M + H) |
|---|---|---|---|
| 4 | 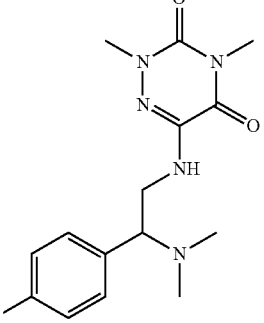<br>6-((2-(dimethylamino)-2-(4-fluorophenyl)ethyl)amino)-2,4-dimethyl-1,2,4-triazine-3,5(2H,4H)-dione | ¹H NMR (500 MHz, DMSO-d6) δ 7.31 (dd, J = 5.63, 8.65 Hz, 2H), 7.10-7.18 (m, 2H), 6.17 (t, J = 5.22 Hz, 1H), 3.72 (t, J = 7.00 Hz, 1H), 3.52- 3.57 (m, 1H), 3.36 (s, 3H), 3.31-3.33 (m, 1H), 3.15 (s, 3H), 2.08 (s, 6H). (Racemic mixture) | 322 |
| 5 | 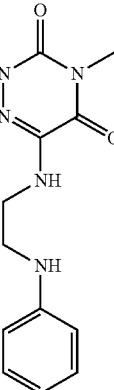<br>2,4-dimethyl-6-((2-(phenylamino)ethyl)amino)- | ¹H NMR (500 MHz, DMSO-d6) δ 7.05 (dd, J = 7.42, 8.24 Hz, 2H), 6.75 (t, J = 5.77 Hz, 1H), 6.60 (d, J = 7.69 Hz, 2H), 6.50 (t, J = 7.28 Hz, 1H), 5.66 (t, J = 5.77 Hz, 1H), 3.37 (s, 3H), 3.26-3.30 (m, 2H), 3.18-3.22 (m, 2H), 3.17 (s, 3H) | 276 |

-continued

| Example | Compound Name | NMR | M/Z (M + H) |
|---------|---------------|-----|-------------|
|  | 1,2,4-triazine-3,5(2H,4H)-dione | | |
| 6 | 6-((2-(dimethylamino)-2-(4-methoxyphenyl)ethyl)amino)-2,4-dimethyl-1,2,4-triazine-3,5(2H,4H)-dione | $^1$H NMR (500 MHz, DMSO-d6) δ 7.18 (d, J = 8.51 Hz, 2H), 6.89 (d, J = 8.51 Hz, 2H), 5.93-6.18 (m, 1H), 3.73 (s, 3H), 3.63-3.67 (m, 1H), 3.49-3.55 (m, 1H), 3.35 (s, 3H), 3.30-3.34 (m, 1H), 3.16 (s, 3H), 2.07 (s, 6H). (Racemic mixture) | 334 |
| 7 | 6-((2-(dimethylamino)ethyl)(methyl)amino)-2,4-dimethyl-1,2,4-triazine-3,5(2H,4H)-dione (trifluoroacetic acid salt) | $^1$H NMR (500 MHz, DMSO-d6) δ 9.87 (br. s., 1H), 3.63 (t, J = 6.87 Hz, 2H), 3.41 (s, 3H), 3.32 (t, J = 5.49 Hz, 2H), 3.17 (s, 3H), 2.88 (s, 3H), 2.83 (s, 6H) | 242 |
| 8 | 2,4-dimethyl-6-[(2-methyl-3,4-dihydro-1H-isoquinolin-3-yl)methylamino]-1,2,4-triazine-3,5-dione | $^1$H NMR (400 MHz, DMSO-d6) δ 7.14-6.98 (m, 4H), 6.44 (t, J = 5.5 Hz, 1H), 3.77 (d, J = 16.1 Hz, 1H), 3.62 (d, J = 15.9 Hz, 1H), 3.35 (s, 3H), 3.30-3.23 (m, 1H), 3.18 (s, 3H), 3.12 (dt, J = 13.0, 6.2 Hz, 1H), 3.07-2.99 (m, 1H), 2.77 (d, J = 4.9 Hz, 1H), 2.69 (d, J = 7.3 Hz, 1H), 2.36 (s, 3H). (Racemic mixture) | 316 |

-continued

| Example | Compound Name | NMR | M/Z (M + H) |
|---|---|---|---|
| 9 | 6-((2-(benzyl(methyl)amino)ethyl)amino)-2,4-dimethyl-1,2,4-triazine-3,5(2H,4H)-dione | $^1$H NMR (400 MHz, DMSO-d6) δ 7.28 (d, J = 3.6 Hz, 4H), 7.26-7.16 (m, 1H), 6.37 (t, J = 5.7 Hz, 1H), 3.50 (s, 2H), 3.30 (s, 3H), 3.21 (d, J = 6.0 Hz, 2H), 3.19 (s, 3H), 2.54 (d, J = 6.4 Hz, 2H), 2.18 (s, 3H). | 304 |
| 10 | 6-((2-(3-chlorophenyl)-2-(dimethylamino)ethyl)amino)-2,4-dimethyl-1,2,4-triazine-3,5(2H,4H)-dione | $^1$H NMR (400 MHz, DMSO-d6) δ 7.42-7.30 (m, 3H), 7.25 (dt, J = 6.3, 1.8 Hz, 1H), 6.25 (dd, J = 6.4, 4.5 Hz, 1H), 3.72 (t, J = 6.9 Hz, 1H), 3.61-3.48 (m, 1H), 3.44-3.37 (m, 1H), 3.35 (s, 3H), 3.16 (s, 3H), 2.11 (s, 6H). (Racemic mixture) | 338 |
| 11 | 6-((2-(dimethylamino)-3-phenylpropyl)amino)-2,4-dimethyl-1,2,4-triazine-3,5(2H,4H)-dione | $^1$H NMR (400 MHz, DMSO-d6) δ 7.35-7.13 (m, 5H), 6.15 (d, J = 5.1 Hz, 1H), 3.28 (s, 3H), 3.15 (s, 3H), 3.01 (m, 3H), 2.89 (dd, J = 13.0, 3.5 Hz, 1H), 2.42 (dd, J = 13.5, 8.0 Hz, 1H), 2.29 (s, 6H). (Racemic mixture) | 318 |

-continued

| Example | Compound Name | NMR | M/Z (M + H) |
|---|---|---|---|
| 12 | 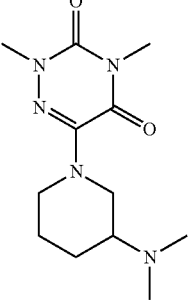<br>6-(3-(dimethylamino)piperidin-1-yl)-2,4-dimethyl-1,2,4-triazine-3,5(2H,4H)-dione | $^1$H NMR (400 MHz, DMSO-d6) δ 4.09-3.98 (m, 1H), 3.91-3.77 (m, 1H), 3.40 (s, 3H), 3.16 (s, 3H), 2.66-2.52 (m, 2H), 2.32 (d, J = 10.6 Hz, 1H), 2.20 (s, 6H), 1.87 (d, J = 10.9 Hz, 1H), 1.78-1.67 (m, 1H), 1.49 (d, J = 12.5 Hz, 1H), 1.41-1.25 (m, 1H). (Racemic mixture) | 268 |
| 13 | 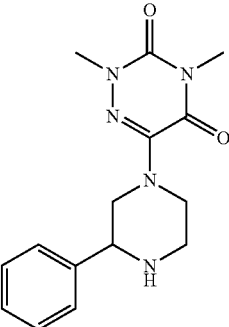<br>2,4-dimethyl-6-(3-phenylpiperazin-1-yl)-1,2,4-triazine-3,5(2H,4H)-dione | $^1$H NMR (400 MHz, DMSO-d6) δ 7.46-7.23 (m, 5H), 4.01-3.77 (m, 3H), 3.39 (s, 3H), 3.16 (s, 3H), 3.00 (s, 2H), 2.82-2.62 (m, 2H). (Racemic mixture) | 302 |
| 14 | 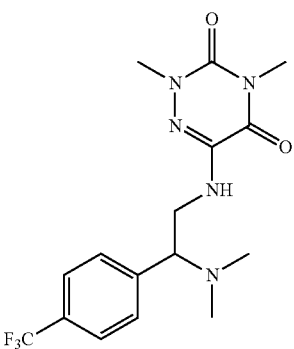 [SMILES: CN(C)C(CNc1nn(C)c(=O)n(C)c1=O)c1ccc(C(F)(F)F)cc1]<br>6-((2-(dimethylamino)-2-(4-(trifluoromethyl)phenyl)ethyl)amino)-2,4-dimethyl-1,2,4-triazine-3,5(2H,4H)-dione | $^1$H NMR (400 MHz, DMSO-d6) δ 7.70 (dd, J = 7.9, 1.1 Hz, 2H), 7.51 (d, J = 8.0 Hz, 2H), 6.30 (d, J = 1.6 Hz, 1H), 3.80 (t, J = 6.8 Hz, 1H), 3.59 (ddd, J = 13.5, 7.0, 4.6 Hz, 1H), 3.45-3.36 (m, 1H), 3.35 (s, 3H), 3.16 (s, 3H), 2.13 (s, 6H). (Racemic mixture) | 372 |

-continued

| Example | Compound Name | NMR | M/Z (M + H) |
|---|---|---|---|
| 15 | 6-((2-(dimethylamino)-2-phenylpropyl)amino)-2,4-dimethyl-1,2,4-triazine-3,5(2H,4H)-dione | $^1$H NMR (400 MHz, DMSO-d6) δ 7.57-7.16 (m, 5H), 5.56 (dd, J = 5.9, 4.1 Hz, 1H), 3.29 (s, 3H), 3.24 (dd, J = 13.2, 6.0 Hz, 1H), 3.13 (s, 3H), 2.14 (s, 6H), 1.36 (s, 3H). (Racemic mixture) | 318 |
| 16 | 2,4-dimethyl-6-((2-phenyl-2-(pyrrolidin-1-yl)ethyl)amino)-1,2,4-triazine-3,5(2H,4H)-dione | $^1$H NMR (400 MHz, DMSO-d6) δ 7.36-7.14 (m, 5H), 6.07 (s, 1H), 3.55 (d, J = 2.8 Hz, 2H), 3.40-3.34 (m, 1H), 3.33 (s, 3H), 3.14 (s, 3H), 2.48 (s, 2H), 2.38 (dd, J = 7.1, 2.5 Hz, 2H), 1.65 (d, J = 5.7 Hz, 4H). (Racemic mixture) | 330 |
| 17 | 6-(((1S,2S)-1-(dimethylamino)-1-phenylpropan-2-yl)amino)-2,4-dimethyl-1,2,4-triazine-3,5(2H,4H)-dione | $^1$H NMR (400 MHz, DMSO-d6) δ 7.28-7.42 (m, 3H), 7.20-7.26 (m, 2H), 6.31 (d, J = 3.96 Hz, 1H), 3.95-4.06 (m, 1H), 3.56 (d, J = 10.14 Hz, 1H), 3.41 (s, 3H), 3.21 (s, 3H), 2.02 (s, 6H), 0.96 (d, J = 6.18 Hz, 3H). (Racemic mixture; unknown relative stereochemistry; and single diastereoisomer) | 318 |

Example 18

The following compound was prepared in a similar fashion to Example 1, using dimethylacetamide at 180° C. instead of isopropanol at 150° C. The Intermediate C was used as reactant.

| Example | Compound Name | NMR | M/Z (M + H) |
|---|---|---|---|
| 18 | 6-(((1S,2S)-1-(dimethylamino)-1-(4-(phenylsulfonyl)phenyl)propan-2-yl)amino)-2,4-dimethyl-1,2,4-triazine-3,5(2H,4H)-dione | ¹H NMR (400 MHz, DMSO-d6) δ 7.95-8.00 (m, 4H), 7.64-7.71 (m, 3H), 7.49 (m, J = 8.3 Hz, 2H), 6.25 (d, J = 4.8 Hz, 1H), 4.04-4.08 (m, 1H), 3.67 (d, J = 9.4 Hz, 1H), 3.40 (s, 3H), 3.20 (s, 3H), 2.01 (s, 6H), 0.90 (d, J = 6.2 Hz, 3H). (Racemic mixture; unknown relative stereochemistry; and single diastereoisomer) | 458 |

Example 19

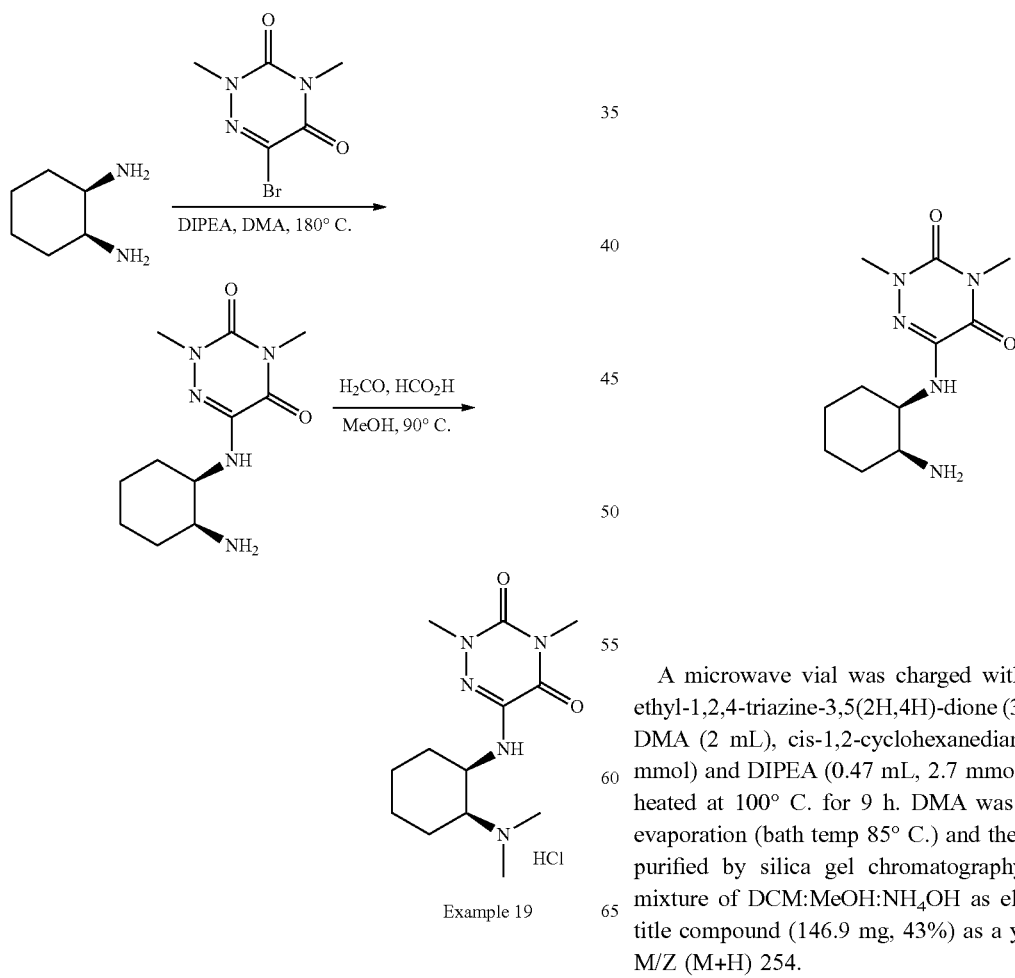

Example 19

Step 1

6-butoxy-2,4-dimethyl-1,2,4-triazine-3,5(2H,4H)-dione

A microwave vial was charged with 6-bromo-2,4-dimethyl-1,2,4-triazine-3,5(2H,4H)-dione (300 mg, 1.36 mmol), DMA (2 mL), cis-1,2-cyclohexanediamine (0.33 mL, 2.7 mmol) and DIPEA (0.47 mL, 2.7 mmol). The reaction was heated at 100° C. for 9 h. DMA was removed by rotary evaporation (bath temp 85° C.) and the crude material was purified by silica gel chromatography using a 95:5:0.5 mixture of DCM:MeOH:NH₄OH as eluent to provide the title compound (146.9 mg, 43%) as a yellow solid. LCMS M/Z (M+H) 254.

Step 2

6-((2-(dimethylamino)cyclohexyl)amino)-2,4-dimethyl-1,2,4-triazine-3,5(2H,4H)-dione hydrochloride

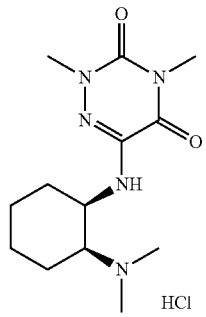 [SMILES: CN(C)[C@H]1CCCC[C@H]1Nc1nn(C)c(=O)n(C)c1=O ; Cl]

In a 25 mL round bottom flask 6-((2-aminocyclohexyl)amino)-2,4-dimethyl-1,2,4-triazine-3,5(2H,4H)-dione (0.146 g, 0.58 mmol) was dissolved in EtOH (7 mL). Formaldehyde (37% in water, 1.5 mL) and formic acid (88%, 1.5 mL) were added and the reaction was heated at 90° C. overnight. The reaction was cooled to ambient temperature, poured into sat. aq. $NaHCO_3$ and extracted with DCM (3×). The combined organic layer was washed with brine, dried over $Na_2SO_4$, filtered, concentrated and purified by silica gel chromatography using isocratic 55% 90:10:1 DCM:MeOH:$NH_4OH$ mixing with DCM as eluent. The product fractions were concentrated then treated with 4M HCl in dioxane (5 mL), this solution was concentrated under vacuum overnight to provide the title compound (141 mg, 77%) as an off-white solid. $^1H$ NMR (400 MHz, DMSO-d6) δ 9.90 (s, 1H), 6.05 (d, J=9.4 Hz, 1H), 4.40 (d, J=9.0 Hz, 1H), 3.39 (s, 3H), 3.32-3.27 (m, 1H), 3.21 (s, 3H), 2.76 (dd, J=4.7, 16.3 Hz, 6H), 2.03 (br. s., 1H), 1.97-1.89 (m, 1H), 1.80 (t, J=10.9 Hz, 2H), 1.46-1.21 (m, 4H). LCMS M/Z (M+H) 282. (Racemic mixture; single known diastereoisomer)

Example 20

The following compound was prepared in a similar fashion to Example 19, using trans-1,2-cyclohexanediamine instead of cis-1,2-cyclohexanediamine.

| Example | Compound Name | NMR | M/Z (M + H) |
|---|---|---|---|
| 20 | 6-(((1R,2R)-2-(dimethylamino)cyclohexyl)amino)-2,4-dimethyl-1,2,4-triazine-3,5(2H,4H)-dione | $^1H$ NMR (400 MHz, DMSO-d6) δ 6.17 (d, J = 3.7 Hz, 1H), 3.35 (s, 3H), 3.28-3.21 (m, 1H), 3.18 (s, 3H), 2.48-2.36 (m, 2H), 2.19-2.10 (m, 6H), 1.85-1.70 (m, 2H), 1.62 (d, J = 8.3 Hz, 1H), 1.28-1.00 (m, 4H). (Racemic mixture; single known diastereoisomer) | 282 |

Example 21

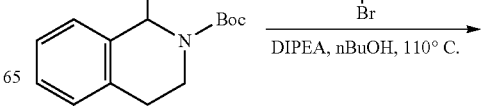

-continued

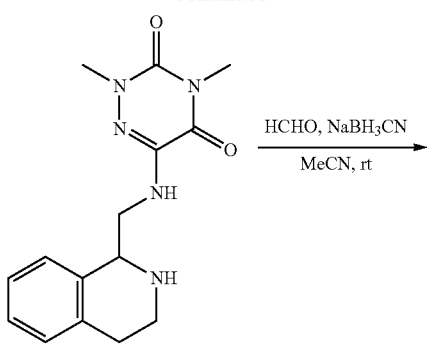

Example 21

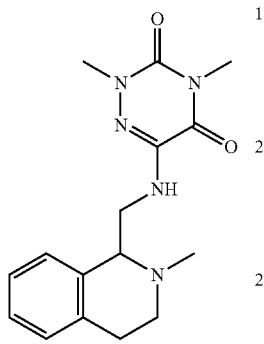

Step 1

2,4-dimethyl-6-(((1,2,3,4-tetrahydroisoquinolin-1-yl)methyl)amino)-1,2,4-triazine-3,5(2H,4H)-dione (Racemic Mixture)

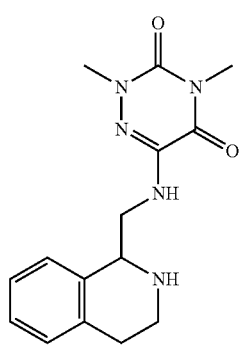 [SMILES: Cn1nc(NCC2NCCc3ccccc32)c(=O)n(C)c1=O]

To a solution of tert-butyl 1-(aminomethyl)-3,4-dihydroisoquinoline-2(1H)-carboxylate (Intermediate E, 200 mg, 0.76 mmol) in a nBuOH (4 mL) was added 6-bromo-2,4-dimethyl-1,2,4-triazine-3,5(2H,4H)-dione (184 mg, 0.84 mmol) and N-ethyl-N-isopropylpropan-2-amine (197 mg, 1.52 mmol). The mixture was heated at 110° C. under microwave condition for 1 h, at which time LCMS indicated the reaction had gone to completion. The solvent was removed under reduced pressure, and the crude product was purified by silica gel chromatography (DCM:MeOH=10:1) to give the title compound (180 mg, 59% yield) as a light yellow oil. LCMS M/Z (M+H) 302.

Step 2

2,4-dimethyl-6-(((2-methyl-1,2,3,4-tetrahydroisoquinolin-1-yl)methyl)amino)-1,2,4-triazine-3,5(2H,4H)-dione (Racemic Mixture)

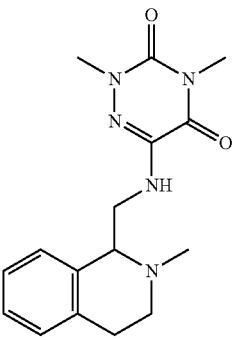 [SMILES: CN1CCc2ccccc2C1CNc1nn(C)c(=O)n(C)c1=O]

To a solution of 2,4-dimethyl-6-(((1,2,3,4-tetrahydroisoquinolin-1-yl)methyl)amino)-1,2,4-triazine-3,5(2H,4H)-dione (200 mg, 0.663 mmol) in MeCN (10 mL) was added 30% aqueous formaldehyde (2 mL) and NaBH$_3$CN (125 mg, 1.99 mmol). The mixture was stirred at ambient temperature for 2 h, at which time LCMS showed the completion of the reaction. The reaction was quenched by addition of 2 N HCl solution and the solvent was evaporated under reduced pressure. The residue was dissolved in ethyl acetate (30 mL) and washed with saturated aqueous NaHCO$_3$ (20 mL). The separated organic layer was concentrated under reduced pressure and the crude product was purified by reverse phase chromatography (acetonitrile 40-70%/0.1% NH$_4$OH in water) to give the title compound (20 mg, 10% yield) as a white solid. $^1$H NMR (400 MHz, DMSO-d6) δ 7.25-7.22 (m, 1H), 7.14-7.09 (m, 3H), 6.12-6.09 (m, 1H), 3.75-3.72 (m, 1H), 3.38-3.33 (m, 5H), 3.16 (s, 3H), 3.15-3.10 (m, 1H), 2.81-2.76 (m, 1H), 2.68-2.59 (m, 2H), 2.42 (s, 3H). LCMS M/Z (M+H) 316.

Example 22

6-((2-(dimethylamino)-2-phenylethyl)amino)-2,4-diethyl-1,2,4-triazine-3,5(2H,4H)-dione (Racemic Mixture)

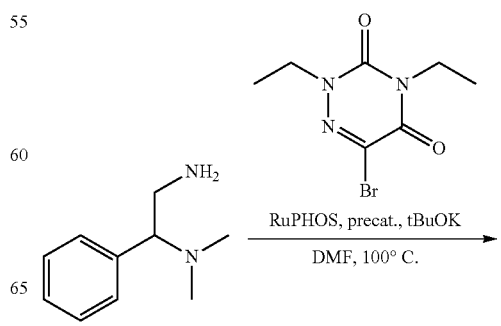

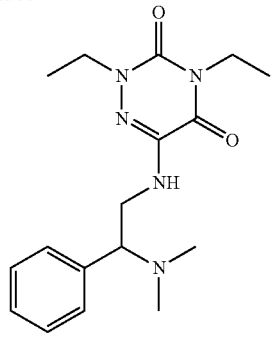

Example 22

A mixture of 6-bromo-2,4-dimethyl-1,2,4-triazine-3,5 (2H,4H)-dione (Intermediate B, 300 mg, 1.36 mmol), N,N-dimethyl-1-phenylethane-1,2-diamine (336 mg, 2.05 mmol), t-BuOK (306 mg, 2.73 mmol) and Ruphos $3^{rd}$ generation precatalyst (30 mg, 0.04 mmol) in DMF (8 mL) was heated at 100° C. under microwave conditions for 2 h under $N_2$, at which time LCMS indicated the reaction had reached completion. The reaction mixture was poured into water (5 mL), and then extracted with ethyl acetate (3×10 mL). The combined organic extracts were dried over $Na_2SO_4$ and concentrated under reduced pressure. The residue was purified by reverse phase chromatography (acetonitrile 30-65%/0.1% $NH_4OH$ in water) to give the title compound (8 mg, 2% yield) as a white solid. $^1$H NMR (400 MHz, Methanol-d4) δ 7.39-7.29 (m, 5H), 3.97-3.59 (m, 7H), 2.29 (s, 6H), 1.31-1.27 (m, 3H), 1.21-1.17 (m, 3H). LCMS M/Z (M+H) 332.

Biological Data

IC$_{50}$ Measurements for Inhibitors Using PCAF AlphaLisa Binding Assay

His/Flag epitope tagged PCAF$_{719-832}$ bromodomain was cloned, expressed and purified to homogeneity in-house. PCAF bromodomain binding and inhibition of the compounds disclosed herein was assessed by monitoring the engagement of biotinylated small molecule ligand (known to bind to the PCAF bromodomain) with the target using the AlphaLisa technology (Perkin-Elmer). Specifically, in a 384 well ProxiPlate PCAF bromodomain (225 nM final) was combined with the biotinylated small molecule ligand (6 nM final) in 50 mM HEPES (pH 7.5), 75 mM NaCl, 1 mM TCEP, 0.01% (w/v) BSA, and 0.008% (w/v) Brij-35 either in the presence of DMSO (final 0.2% DMSO) or compound dilution series in DMSO. After 15 minute incubation at room temperature AlphaLisa streptavidin acceptor beads and AlphaLisa anti-histidine donor beads were added to a final concentration of 12.5 µg/mL each. After 90 minutes of equilibration plates were read on an Envision instrument and IC$_{50}$s calculated using a four parameter non-linear curve fit.

PCAF IC$_{50}$ values for the Examples 1-22 were determined using the general procedure described above.

| Example | PCAF IC$_{50}$ (µM) |
| --- | --- |
| 1 | >20 |
| 2 | >20 |
| 3 | 2.5 |
| 4 | 0.28 |
| 5 | 65 |
| 6 | 0.15 |
| 7 | 37 |
| 8 | 0.38 |
| 9 | 7.5 |
| 10 | 0.43 |
| 11 | 1.4 |
| 12 | >20 |
| 13 | >20 |
| 14 | 0.25 |
| 15 | 0.48 |
| 16 | 8.1 |
| 17 | 0.12 |
| 18 | 0.070 |
| 19 | 1.1 |
| 20 | 0.23 |
| 21 | 1.2 |
| 22 | 12 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I), or a salt thereof:

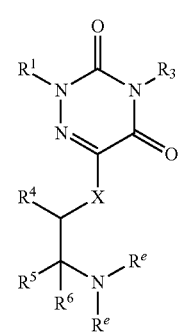

(I)

wherein:

R$^1$ is selected from the group consisting of C$_{1-6}$alkyl, C$_{2-6}$alkenyl, C$_{2-6}$alkynyl, and carbocyclyl;

R$^3$ is selected from the group consisting of C$_{1-6}$alkyl, C$_{2-6}$alkenyl, C$_{2-6}$alkynyl, and carbocyclyl;

and the group:

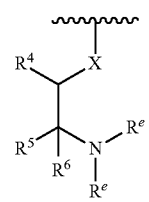

is selected from the group consisting of:

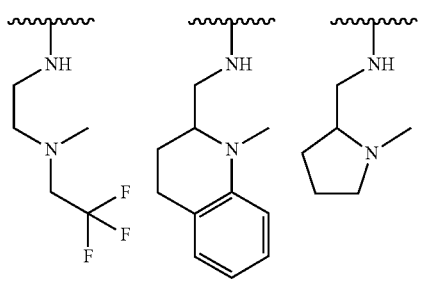
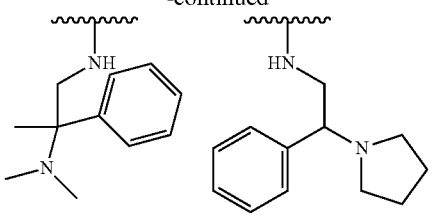
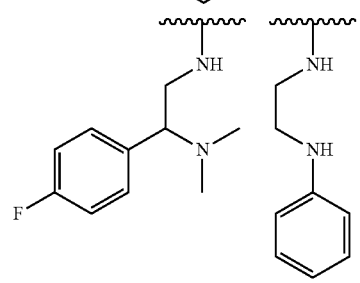
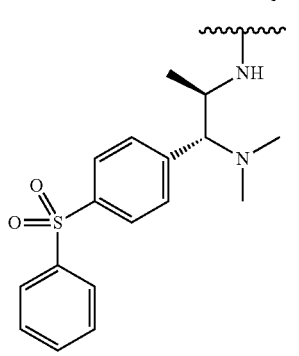
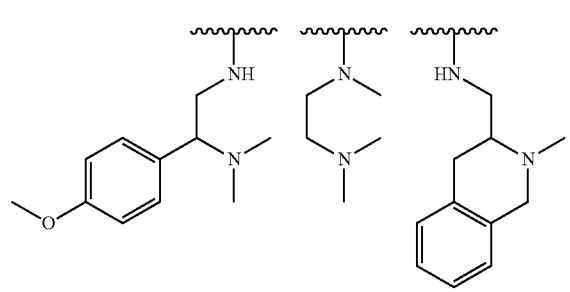
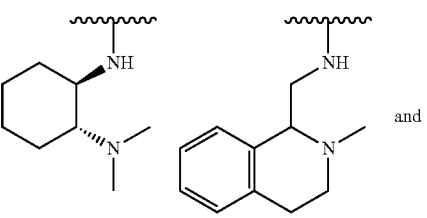
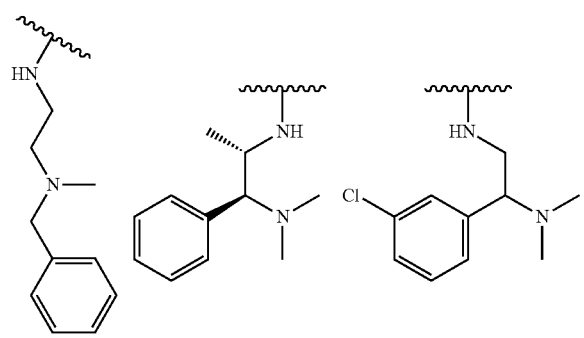
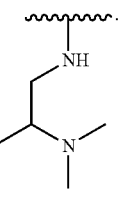
provided that when $R^1$ is methyl, $R^3$ is methyl, X is N(H), $R^4$ is H, $R^6$ is H and each Re is $CH_3$;
then $R^5$ is not phenyl; and
provided the compound is not:
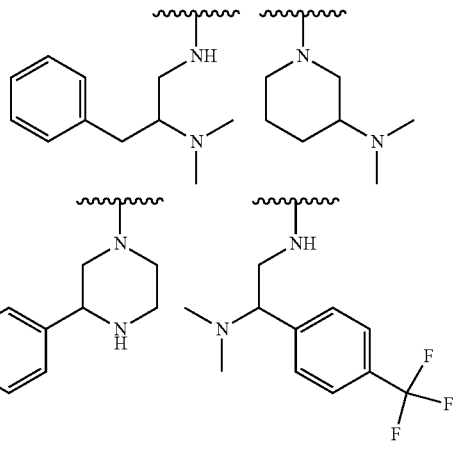
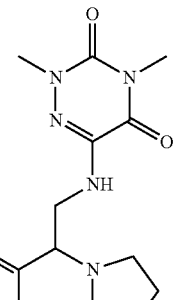
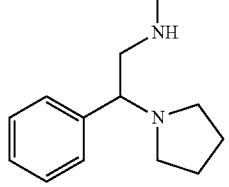
or a salt thereof.

2. The compound of claim 1 wherein the group:
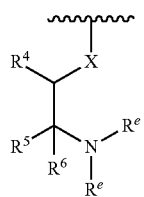
is selected from the group consisting of:
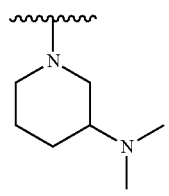 and 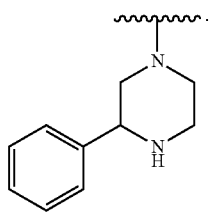
3. The compound or salt of claim 1, which is selected from the group consisting of:
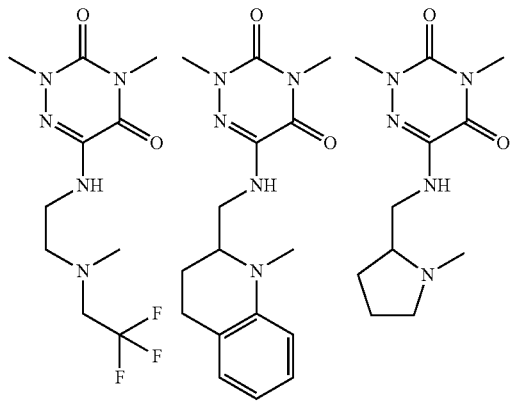
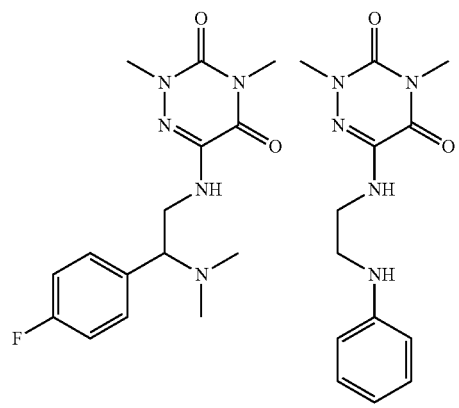
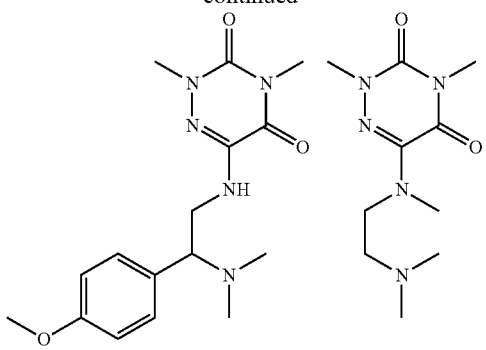
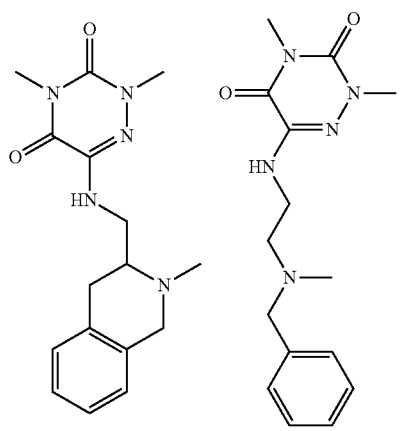
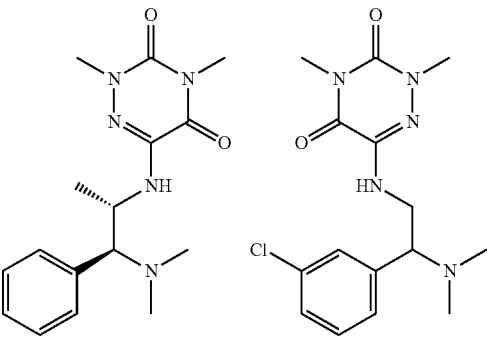
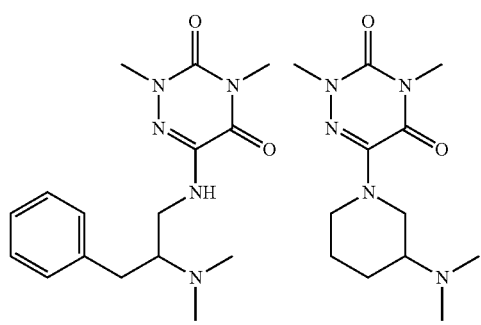

-continued

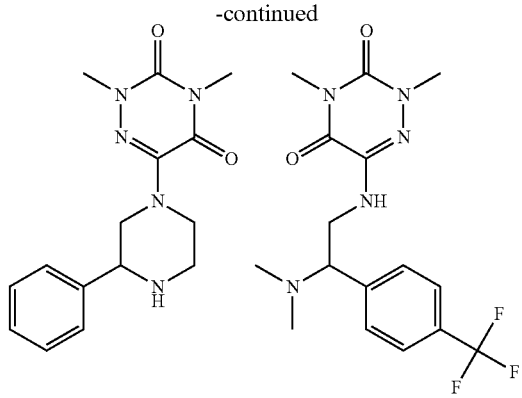

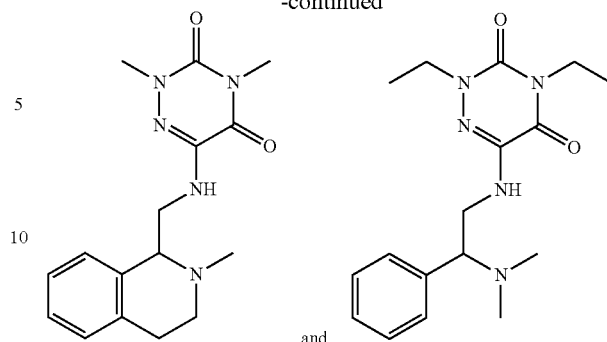

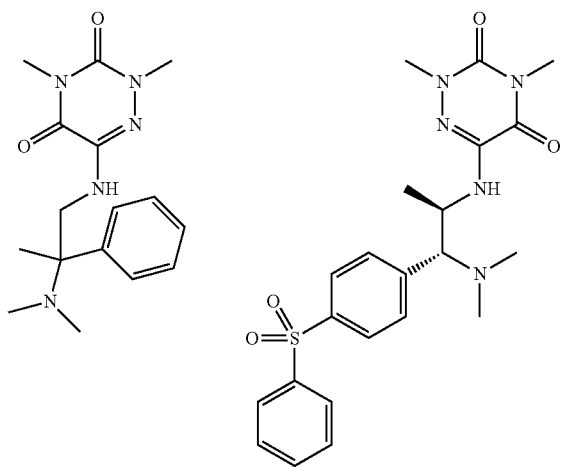

or a salt thereof.

4. A composition comprising a compound of claim 1, or a pharmaceutically acceptable salt thereof and a pharmaceutically acceptable adjuvant, carrier, or vehicle.

5. A method for treating ovarian cancer or renal cell carcinoma in an animal comprising administering to the animal a compound of claim 1 or a pharmaceutically acceptable salt thereof.

6. A method of treating ovarian cancer or renal cell carcinoma in an individual comprising administering to the individual (a) a compound of claim 1 or a pharmaceutically acceptable salt thereof, and (b) a cytotoxic agent.

7. The compound of claim 1, wherein $R^1$ is methyl.

8. The compound of claim 1, wherein $R^3$ is methyl.

9. A method of treating ovarian cancer or renal cell carcinoma in an animal comprising administering to the animal a compound of formula:

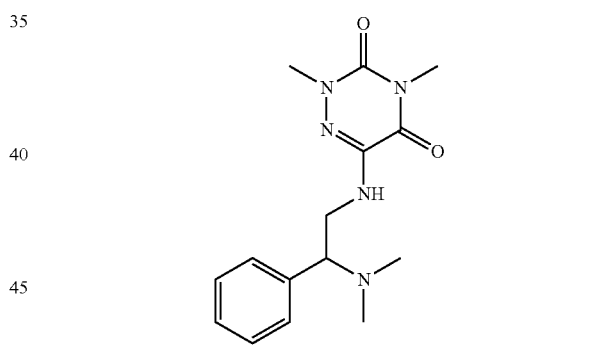

or a pharmaceutically acceptable salt thereof.

* * * * *

UNITED STATES PATENT AND TRADEMARK OFFICE
CERTIFICATE OF CORRECTION

PATENT NO. : 10,358,437 B2
APPLICATION NO. : 15/449706
DATED : July 23, 2019
INVENTOR(S) : Brian K. Albrecht et al.

Page 1 of 1

It is certified that error appears in the above-identified patent and that said Letters Patent is hereby corrected as shown below:

In the Claims

Column 74, Lines 47, Claim 1, please delete "each Re is $CH_3$;" and insert -- each $R^e$ is $CH_3$; -- therefor.

Signed and Sealed this
Twelfth Day of November, 2019

Andrei Iancu
*Director of the United States Patent and Trademark Office*